US008591916B2

(12) United States Patent
Delagrave et al.

(10) Patent No.: US 8,591,916 B2
(45) Date of Patent: Nov. 26, 2013

(54) FLAVIVIRUS VACCINE VECTOR AGAINST INFLUENZA VIRUS

(75) Inventors: Simon Delagrave, Stoneham, MA (US); Farshad Guirakhoo, Chaponost (FR); Caroline Maier, Marseilles (FR); Alexander A. Rumyantsev, Somerville, MA (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 523 days.

(21) Appl. No.: 12/525,168

(22) PCT Filed: Jan. 31, 2008

(86) PCT No.: PCT/US2008/001309
§ 371 (c)(1),
(2), (4) Date: May 27, 2010

(87) PCT Pub. No.: WO2008/115314
PCT Pub. Date: Sep. 25, 2008

(65) Prior Publication Data
US 2010/0255028 A1 Oct. 7, 2010

Related U.S. Application Data

(60) Provisional application No. 60/898,651, filed on Jan. 31, 2007.

(51) Int. Cl.
*A61K 39/12* (2006.01)
*C07H 21/02* (2006.01)

(52) U.S. Cl.
USPC .................... 424/218.1; 424/199.1; 435/69.1; 536/23.72

(58) Field of Classification Search
None
See application file for complete search history.

(56) References Cited

U.S. PATENT DOCUMENTS

| | | | | |
|---|---|---|---|---|
| 5,719,051 | A * | 2/1998 | Mundt et al. | 435/235.1 |
| 6,309,650 | B1 | 10/2001 | Kim et al. | |
| 6,497,884 | B1 * | 12/2002 | Pletnev et al. | 424/218.1 |
| 6,685,948 | B1 * | 2/2004 | Zeng et al. | 424/218.1 |
| 6,893,866 | B1 * | 5/2005 | Westaway et al. | 435/320.1 |
| 8,029,802 | B2 * | 10/2011 | Guirakhoo et al. | 424/218.1 |
| 2003/0044773 | A1 | 3/2003 | Kleanthous et al. | |

FOREIGN PATENT DOCUMENTS

| | | | |
|---|---|---|---|
| WO | WO 02/102828 | A2 | 12/2002 |
| WO | WO 2006/044857 | A2 * | 4/2006 |
| WO | WO 2006/116182 | A1 | 11/2006 |

OTHER PUBLICATIONS

Ebrahimi et al., Virus Genes, 2011, 42:1-9.*
Kuno et al., In Vitro Cellular and Developmental Biology, Feb. 1989, 26(2):193-196.*
Fiers et al., Virus Research, 2004, 103:173-176.*
Wu et al., "Characterization of Immunity Induced by M2e of Influenza Virus," Vaccine 25:8868-8873, 2007.
Bonaldo et al., "Expression of Foreign Protein Epitopes at the Surface of Recombinant Yellow Fever 17D Viruses Based on Three-Dimensional Modeling of its Envelope Protein," Cell Biochem. Biophys. 44:313-324, 2006.
Jones et al., "Construction and Applications of Yellow Fever Virus Replicons," Virology 331:247-259, 2005.
Kim et al., "Study on Persistent Infection of Japanese Encephalitis Virus Beijing-1 Strain in Serum-Free Sf9 Cell Cultures," J. Microbiol. 42:25-31, 2004.
Wechuck et al., "Effect of Temperature, Medium Composition, and Cell Passage on Production of Herpes-Based Viral Vectors," Biotechnology and Bioengineering 79:112-119, 2002.
Zou et al., "The Epitope Recognized by a Monoclonal Antibody in Influenza A Virus M2 Protein is Immunogenic and Confers Immune Protection," Int. Immunopharmacol. 5:631-635, 2005.
XP-002582379, Database UniProtKB/TrEMBL, Q99DQ9 (online) "Polyprotein" Jun. 1, 2001.
Extended European Search Report from European Application No. EP 08799654, dated Jun. 9, 2010 (date of completion of search) and Jun. 17, 2010 (date of mailing of report).
International Preliminary Report on Patentability from International Application No. PCT/US2008/001309, dated Sep. 8, 2009.
Bonaldo et al., "Attenuation of Recombinant Yellow Fever 17D Viruses Expressing Foreign Protein Epitopes at the Surface," J. Virol. 79:8602-8613, 2005.
Mandl et al., "Antigenic Structure of the Flavivirus Envelope Protein E at the Molecular Level, Using Tick-Borne Encephalitis Virus as a Model," J. Virol. 63:564-571, 1989.
Wu et al., "Structural Basis of a Flavivirus Recognized by its Neutralizing Antibody," J. Biol. Chem. 278:46007-46013, 2003.
International Search Report from International Application No. PCT/US2008/001309, dated May 28, 2009 (date of completion of search), and Jun. 10, 2009 (date of mailing of report).
Written Opinion from International Application No. PCT/US2008/001309 dated May 28, 2009 (date of completion of opinion), and Jun. 10, 2009 (date of mailing of opinion).

* cited by examiner

*Primary Examiner* — Stacy B. Chen
(74) *Attorney, Agent, or Firm* — Clark & Elbing LLP

(57) ABSTRACT

This invention relates to chimeric flavivirus vectors that can be used, for example, in the prevention and treatment of influenza virus infection, compositions including such viral vectors, and methods employing the vectors.

19 Claims, 10 Drawing Sheets

Figure 1

Identification of M2e insert sites in E protein based on flavivirus multiple alignment and structure based analysis TBEV 195 AQTVILELDKTVEHLPTAWQVHRDWFND 222
YFV  191 GNSYIAEMET------ESWIVDRQWAQD 212
WNV  199 NAYYVMTVGT------KTFLVHREWFMD 220
DEN4 194 NEMILMKKK-------KTWLVHKQWFLD 215
JEV  199 EAFYVMTVGS------KSFLVHREWFHD 220

TBEV 270 G---VPVAHIEGTKYHLKSGHVTC 290
YFV  260 GAMRVTKDTNDNNLYKLHGGHVSC 283
WNV  268 G---AIPVEFSSNTVKLTSGHLKC 288
DEN4 266 G---ATEVDSGD-GNHMFAGHLKC 285
JEV  268 G---AIVEYSS-SVKLTSGHLKC  287

GMSLLTEVETPIRGG

GGMSLLTEVETPIRNEWGSRSNDSSDGG
or GGMSLLTEVETPIRGG

With the primer pair JE1.474+ and JE 2.5- chosen for RT-PCR we have:

-fragment of 212 bp if no M2e insert
-fragment of 257 bp if there is M2e insert

Figure 5

Stability of M2e insert at E277 of CVJE

E277M2e-P2 → [10 Vero passages 37°C, 0.001 MOI] → E277M2e-P12

Neutralization of E277M2e-P2 and CVJE parent with αM2 Mab 14C2

| Virus | PRNT$_{50}$ antibody dilution | |
|---|---|---|
| | 14C2 Mab | αAcam-FluA Pab |
| CVJE | <200 | <20 |
| E277M2e-P2 | ≥819,200 | ≥81,920 |

Immunogenicity of E277M2e-P2 virus in mice

SEQUENCE LISTING

<160> NUMBER OF SEQ ID NOS: 76

<210> SEQ ID NO 1
<211> LENGTH: 12
<212> TYPE: PRT
<213> ORGANISM: Influenza virus

<400> SEQUENCE: 1

Met Ser Leu Leu Thr Glu Val Glu Thr Pro Ile Arg
1               5                   10

<210> SEQ ID NO 2
<211> LENGTH: 24
<212> TYPE: PRT
<213> ORGANISM: Influenza virus -continued

```
<400> SEQUENCE: 2

Met Ser Leu Leu Thr Glu Val Glu Thr Pro Ile Arg Asn Glu Trp Gly
1               5                   10                  15

Ser Arg Ser Asn Asp Ser Ser Asp
            20

<210> SEQ ID NO 3
<211> LENGTH: 28
<212> TYPE: PRT
<213> ORGANISM: Tick-borne encephalitis virus

<400> SEQUENCE: 3

Ala Gln Thr Val Ile Leu Glu Leu Asp Lys Thr Val Glu His Leu Pro
1               5                   10                  15

Thr Ala Trp Gln Val His Arg Asp Trp Phe Asn Asp
            20                  25

<210> SEQ ID NO 4
<211> LENGTH: 22
<212> TYPE: PRT
<213> ORGANISM: Yellow fever virus

<400> SEQUENCE: 4

Gly Asn Ser Tyr Ile Ala Glu Met Glu Thr Glu Ser Trp Ile Val Asp
1               5                   10                  15

Arg Gln Trp Ala Gln Asp
            20

<210> SEQ ID NO 5
<211> LENGTH: 22
<212> TYPE: PRT
<213> ORGANISM: West Nile virus

<400> SEQUENCE: 5

Asn Ala Tyr Tyr Val Met Thr Val Gly Thr Lys Thr Phe Leu Val His
1               5                   10                  15

Arg Glu Trp Phe Met Asp
            20

<210> SEQ ID NO 6
<211> LENGTH: 22
<212> TYPE: PRT
<213> ORGANISM: Dengue 4 virus

<400> SEQUENCE: 6

Asn Glu Met Ile Leu Met Lys Met Lys Lys Lys Thr Trp Leu Val His
1               5                   10                  15

Lys Gln Trp Phe Leu Asp
            20

<210> SEQ ID NO 7
<211> LENGTH: 22
<212> TYPE: PRT
<213> ORGANISM: Japanese encephalitis virus

<400> SEQUENCE: 7

Glu Ala Phe Tyr Val Met Thr Val Gly Ser Lys Ser Phe Leu Val His
1               5                   10                  15

Arg Glu Trp Phe His Asp
            20

<210> SEQ ID NO 8
```

```
<211> LENGTH: 21
<212> TYPE: PRT
<213> ORGANISM: Tick-borne encephalitis virus

<400> SEQUENCE: 8

Gly Val Pro Val Ala His Ile Glu Gly Thr Lys Tyr His Leu Lys Ser
1               5                   10                  15

Gly His Val Thr Cys
            20

<210> SEQ ID NO 9
<211> LENGTH: 24
<212> TYPE: PRT
<213> ORGANISM: Yellow fever virus

<400> SEQUENCE: 9

Gly Ala Met Arg Val Thr Lys Asp Thr Asn Asp Asn Asn Leu Tyr Lys
1               5                   10                  15

Leu His Gly Gly His Val Ser Cys
            20

<210> SEQ ID NO 10
<211> LENGTH: 21
<212> TYPE: PRT
<213> ORGANISM: West Nile virus

<400> SEQUENCE: 10

Gly Ala Ile Pro Val Glu Phe Ser Ser Asn Thr Val Lys Leu Thr Ser
1               5                   10                  15

Gly His Leu Lys Cys
            20

<210> SEQ ID NO 11
<211> LENGTH: 20
<212> TYPE: PRT
<213> ORGANISM: Dengue 4 virus

<400> SEQUENCE: 11

Gly Ala Thr Glu Val Asp Ser Gly Asp Gly Asn His Met Phe Ala Gly
1               5                   10                  15

His Leu Lys Cys
            20

<210> SEQ ID NO 12
<211> LENGTH: 20
<212> TYPE: PRT
<213> ORGANISM: Japanese encephalitis virus

<400> SEQUENCE: 12

Gly Ala Ile Val Val Glu Tyr Ser Ser Ser Val Lys Leu Thr Ser Gly
1               5                   10                  15

His Leu Lys Cys
            20

<210> SEQ ID NO 13
<211> LENGTH: 15
<212> TYPE: PRT
<213> ORGANISM: Influenza virus

<400> SEQUENCE: 13

Gly Met Ser Leu Leu Thr Glu Val Glu Thr Pro Ile Arg Gly Gly
1               5                   10                  15
```

```
<210> SEQ ID NO 14
<211> LENGTH: 28
<212> TYPE: PRT
<213> ORGANISM: Influenza virus

<400> SEQUENCE: 14

Gly Gly Met Ser Leu Leu Thr Glu Val Glu Thr Pro Ile Arg Asn Glu
1               5                   10                  15

Trp Gly Ser Arg Ser Asn Asp Ser Ser Asp Gly Gly
            20                  25

<210> SEQ ID NO 15
<211> LENGTH: 16
<212> TYPE: PRT
<213> ORGANISM: Influenza virus

<400> SEQUENCE: 15

Gly Gly Met Ser Leu Leu Thr Glu Val Glu Thr Pro Ile Arg Gly Gly
1               5                   10                  15

<210> SEQ ID NO 16
<211> LENGTH: 17
<212> TYPE: DNA
<213> ORGANISM: Japanese encephalitis virus

<400> SEQUENCE: 16
tggagtactc aagctca                                                    17

<210> SEQ ID NO 17
<211> LENGTH: 17
<212> TYPE: DNA
<213> ORGANISM: Japanese encephalitis virus

<400> SEQUENCE: 17
gtgatgttaa catcagg                                                    17

<210> SEQ ID NO 18
<211> LENGTH: 118
<212> TYPE: DNA
<213> ORGANISM: Artificial
<220> FEATURE:
<223> OTHER INFORMATION: derived from Japanese Encephalitis virus and
      Influenza virus

<400> SEQUENCE: 18
tggagtactc aagctcaggc ggcatgagcc tcctgacaga agtggaaact cccattcgca      60
acgagtgggg gtccagatct aacgattcaa gtgatggggg cgtgatgtta acatcagg      118

<210> SEQ ID NO 19
<211> LENGTH: 40
<212> TYPE: PRT
<213> ORGANISM: Artificial
<220> FEATURE:
<223> OTHER INFORMATION: derived from Japanese Encephalitis virus and
      Influenza virus

<400> SEQUENCE: 19

Val Glu Tyr Ser Ser Ser Gly Gly Met Ser Leu Leu Thr Glu Val Glu
1               5                   10                  15

Thr Pro Ile Arg Asn Glu Trp Gly Ser Arg Ser Asn Asp Ser Ser Asp
            20                  25                  30

Gly Gly Val Met Leu Thr Ser Gly
        35                  40
```

```
<210> SEQ ID NO 20
<211> LENGTH: 19
<212> TYPE: PRT
<213> ORGANISM: Influenza virus

<400> SEQUENCE: 20

Asn Ile Pro Ser Ile Gln Ser Arg Gly Leu Phe Gly Ala Ile Ala Gly
1               5                   10                  15

Phe Ile Glu

<210> SEQ ID NO 21
<211> LENGTH: 19
<212> TYPE: PRT
<213> ORGANISM: Influenza virus

<400> SEQUENCE: 21

Asn Val Pro Glu Lys Gln Thr Arg Gly Ile Phe Gly Ala Ile Ala Gly
1               5                   10                  15

Phe Ile Glu

<210> SEQ ID NO 22
<211> LENGTH: 19
<212> TYPE: PRT
<213> ORGANISM: Influenza virus

<400> SEQUENCE: 22

Pro Ala Lys Leu Leu Lys Glu Arg Gly Phe Phe Gly Ala Ile Ala Gly
1               5                   10                  15

Phe Leu Glu

<210> SEQ ID NO 23
<211> LENGTH: 18
<212> TYPE: PRT
<213> ORGANISM: Influenza virus

<400> SEQUENCE: 23

Ser Lys Ala Phe Ser Asn Cys Tyr Pro Tyr Asp Val Pro Asp Tyr Ala
1               5                   10                  15

Ser Leu

<210> SEQ ID NO 24
<211> LENGTH: 18
<212> TYPE: PRT
<213> ORGANISM: Influenza virus

<400> SEQUENCE: 24

Ser Lys Ala Phe Ser Asn Ser Tyr Pro Tyr Asp Val Pro Asp Tyr Ala
1               5                   10                  15

Ser Leu

<210> SEQ ID NO 25
<211> LENGTH: 20
<212> TYPE: PRT
<213> ORGANISM: Influenza virus

<400> SEQUENCE: 25

Met Asn Asn Ala Thr Phe Asn Tyr Thr Asn Val Asn Pro Ile Ser His
1               5                   10                  15

Ile Arg Gly Ser
            20

<210> SEQ ID NO 26
```

```
<211> LENGTH: 6
<212> TYPE: PRT
<213> ORGANISM: Influenza virus

<400> SEQUENCE: 26

Met Leu Glu Pro Phe Gln
1               5

```
<210> SEQ ID NO 32
<211> LENGTH: 23
<212> TYPE: PRT
<213> ORGANISM: Influenza virus

<400> SEQUENCE: 32

Ser Leu Leu Thr Glu Val Glu Thr Pro Ile Arg Asn Glu Trp Glu Cys
1 5 10 15

Arg Cys Asn Asp Ser Ser Asp
20

<210> SEQ ID NO 33
<211> LENGTH: 15
<212> TYPE: PRT
<213> ORGANISM: Artificial
<220> FEATURE:
<223> OTHER INFORMATION: derived from Influenza virus

<400> SEQUENCE: 33

Gly Met Ser Leu Pro Thr Glu Val Glu Thr Pro Ile Arg Gly Gly
1 5 10 15

<210> SEQ ID NO 34
<211> LENGTH: 8
<212> TYPE: PRT
<213> ORGANISM: Hepatitis C virus

<400> SEQUENCE: 34

Ser Thr Asn Pro Lys Pro Gln Arg
1 5

<210> SEQ ID NO 35
<211> LENGTH: 10
<212> TYPE: PRT
<213> ORGANISM: Hepatitis C virus

<400> SEQUENCE: 35

Tyr Leu Leu Pro Arg Arg Gly Pro Arg Leu
1 5 10

<210> SEQ ID NO 36
<211> LENGTH: 9
<212> TYPE: PRT
<213> ORGANISM: Hepatitis C virus

<400> SEQUENCE: 36

Gly Pro Arg Leu Gly Val Arg Ala Thr
1 5

<210> SEQ ID NO 37
<211> LENGTH: 20
<212> TYPE: PRT
<213> ORGANISM: Hepatitis C virus

<400> SEQUENCE: 37

Tyr Pro Trp Pro Leu Tyr Gly Asn Glu Gly Cys Gly Trp Ala Gly Trp
1 5 10 15

Leu Leu Ser Pro
20

<210> SEQ ID NO 38
<211> LENGTH: 16
<212> TYPE: PRT
<213> ORGANISM: Hepatitis C virus

<400> SEQUENCE: 38

```
Gly Phe Ala Asp Leu Met Gly Tyr Ile Pro Leu Val Gly Ala Pro Leu
1               5                   10                  15

<210> SEQ ID NO 39
<211> LENGTH: 9
<212> TYPE: PRT
<213> ORGANISM: Hepatitis C virus

<400> SEQUENCE: 39

Asp Leu Met Gly Tyr Ile Pro Leu Val
1               5

<210> SEQ ID NO 40
<211> LENGTH: 10
<212> TYPE: PRT
<213> ORGANISM: Hepatitis C virus

<400> SEQUENCE: 40

Leu Leu Ala Leu Leu Ser Cys Leu Thr Val
1               5                   10

<210> SEQ ID NO 41
<211> LENGTH: 20
<212> TYPE: PRT
<213> ORGANISM: Hepatitis C virus

<400> SEQUENCE: 41

Arg Glu Gly Asn Ala Ser Arg Cys Trp Val Ala Val Thr Pro Thr Val
1               5                   10                  15

Ala Thr Arg Asp
            20

<210> SEQ ID NO 42
<211> LENGTH: 9
<212> TYPE: PRT
<213> ORGANISM: Hepatitis C virus

<400> SEQUENCE: 42

Ser Thr Gly Leu Ile His Leu His Gln
1               5

<210> SEQ ID NO 43
<211> LENGTH: 10
<212> TYPE: PRT
<213> ORGANISM: Hepatitis C virus

<400> SEQUENCE: 43

Leu Leu Ala Asp Ala Arg Val Cys Ser Cys
1               5                   10

<210> SEQ ID NO 44
<211> LENGTH: 11
<212> TYPE: PRT
<213> ORGANISM: Hepatitis C virus

<400> SEQUENCE: 44

Cys Trp His Tyr Pro Pro Arg Pro Cys Gly Ile
1               5                   10

<210> SEQ ID NO 45
<211> LENGTH: 10
<212> TYPE: PRT
<213> ORGANISM: Hepatitis C virus

<400> SEQUENCE: 45
```

```
Cys Val Ile Gly Gly Val Gly Asn Asn Thr
1               5                   10

<210> SEQ ID NO 46
<211> LENGTH: 10
<212> TYPE: PRT
<213> ORGANISM: Hepatitis C virus

<400> SEQUENCE: 46

Arg Arg Leu Thr Asp Phe Ala Gln Gly Trp
1               5                   10

<210> SEQ ID NO 47
<211> LENGTH: 8
<212> TYPE: PRT
<213> ORGANISM: Hepatitis C virus

<400> SEQUENCE: 47

Thr Ile Asn Tyr Thr Ile Phe Lys
1               5

<210> SEQ ID NO 48
<211> LENGTH: 27
<212> TYPE: PRT
<213> ORGANISM: Hepatitis C virus

<400> SEQUENCE: 48

Glu Thr His Val Thr Gly Gly Asn Ala Gly Arg Thr Thr Ala Gly Leu
1               5                   10                  15

Val Gly Leu Leu Thr Pro Gly Ala Lys Gln Asn
            20                  25

<210> SEQ ID NO 49
<211> LENGTH: 27
<212> TYPE: PRT
<213> ORGANISM: Hepatitis C virus

<400> SEQUENCE: 49

Ile Gln Leu Ile Asn Thr Asn Gly Ser Trp His Ile Asn Ser Thr Ala
1               5                   10                  15

Leu Asn Cys Asn Glu Ser Leu Asn Thr Gly Trp
            20                  25

<210> SEQ ID NO 50
<211> LENGTH: 20
<212> TYPE: PRT
<213> ORGANISM: Hepatitis C virus

<400> SEQUENCE: 50

Leu Phe Tyr Gln His Lys Phe Asn Ser Ser Gly Cys Pro Glu Arg Leu
1               5                   10                  15

Ala Ser Cys Arg
            20

<210> SEQ ID NO 51
<211> LENGTH: 36
<212> TYPE: PRT
<213> ORGANISM: Hepatitis C virus

<400> SEQUENCE: 51

Pro Ser Pro Val Val Val Gly Thr Thr Asp Arg Ser Gly Ala Pro Thr
1               5                   10                  15

Tyr Ser Trp Gly Ala Asn Asp Thr Asp Val Phe Val Leu Asn Asn Thr
```

```
                    20                  25                  30

Arg Pro Pro Leu
        35

<210> SEQ ID NO 52
<211> LENGTH: 6
<212> TYPE: PRT
<213> ORGANISM: Hepatitis C virus

<400> SEQUENCE: 52

Ile Gln Leu Ile Asn Thr
1               5

<210> SEQ ID NO 53
<211> LENGTH: 7
<212> TYPE: PRT
<213> ORGANISM: Human papilloma virus-16

<400> SEQUENCE: 53

Asp Arg Ala His Tyr Asn Ile
1               5

<210> SEQ ID NO 54
<211> LENGTH: 9
<212> TYPE: PRT
<213> ORGANISM: Human papilloma virus-16

<400> SEQUENCE: 54

Arg Ala His Tyr Asn Ile Val Thr Phe
1               5

<210> SEQ ID NO 55
<211> LENGTH: 5
<212> TYPE: PRT
<213> ORGANISM: Human papilloma virus-16

<400> SEQUENCE: 55

Glu Tyr Met Leu Asp
1               5

<210> SEQ ID NO 56
<211> LENGTH: 4
<212> TYPE: PRT
<213> ORGANISM: Human papilloma virus-16

<400> SEQUENCE: 56

Ile Asp Gly Pro
1

<210> SEQ ID NO 57
<211> LENGTH: 5
<212> TYPE: PRT
<213> ORGANISM: Human papilloma virus-16

<400> SEQUENCE: 57

Gln Ala Glu Pro Asp
1               5

<210> SEQ ID NO 58
<211> LENGTH: 11
<212> TYPE: PRT
<213> ORGANISM: Human papilloma virus-18

<400> SEQUENCE: 58

Val Asn His Gln His Leu Pro Ala Arg Arg Ala
```

<210> SEQ ID NO 59
<211> LENGTH: 10
<212> TYPE: PRT
<213> ORGANISM: Human papilloma virus-18

<400> SEQUENCE: 59

Asp Asp Leu Arg Ala Phe Gln Gln Leu Phe
1               5                   10

<210> SEQ ID NO 60
<211> LENGTH: 500
<212> TYPE: PRT
<213> ORGANISM: Japanese encephalitis virus

<400> SEQUENCE: 60

Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Glu Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Ile Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Ser Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Ala Asp Thr Gly His Gly
305                 310                 315                 320

```
Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ala Asn Ser
        355                 360                 365

Lys Val Leu Val Glu Met Glu Pro Pro Phe Gly Asp Ser Tyr Ile Val
370                 375                 380

Val Gly Arg Gly Asp Lys Gln Ile Asn His His Trp His Lys Ala Gly
385                 390                 395                 400

Ser Thr Leu Gly Lys Ala Phe Ser Thr Thr Leu Lys Gly Ala Gln Arg
                405                 410                 415

Leu Ala Ala Leu Gly Asp Thr Ala Trp Asp Phe Gly Ser Ile Gly Gly
            420                 425                 430

Val Phe Asn Ser Ile Gly Lys Ala Val His Gln Val Phe Gly Gly Ala
        435                 440                 445

Phe Arg Thr Leu Phe Gly Gly Met Ser Trp Ile Thr Gln Gly Leu Met
450                 455                 460

Gly Ala Leu Leu Leu Trp Met Gly Val Asn Ala Arg Asp Arg Ser Ile
465                 470                 475                 480

Ala Leu Ala Phe Leu Ala Thr Gly Gly Val Leu Val Phe Leu Ala Thr
                485                 490                 495

Asn Val His Ala
            500

<210> SEQ ID NO 61
<211> LENGTH: 496
<212> TYPE: PRT
<213> ORGANISM: Tick-borne encephalitis virus

<400> SEQUENCE: 61

Ser Arg Cys Thr His Leu Glu Asn Arg Asp Phe Val Thr Gly Thr Gln
1               5                   10                  15

Gly Thr Thr Arg Val Thr Leu Val Leu Glu Leu Gly Gly Cys Val Thr
            20                  25                  30

Ile Thr Ala Glu Gly Lys Pro Ser Met Asp Val Trp Leu Asp Ala Ile
        35                  40                  45

Tyr Gln Glu Asn Pro Ala Lys Thr Arg Glu Tyr Cys Leu His Ala Lys
    50                  55                  60

Leu Ser Asp Thr Lys Val Ala Ala Arg Cys Pro Thr Met Gly Pro Ala
65                  70                  75                  80

Thr Leu Ala Glu Glu His Gln Gly Gly Thr Val Cys Lys Arg Asp Gln
                85                  90                  95

Ser Asp Arg Gly Trp Gly Asn His Cys Gly Leu Phe Gly Lys Gly Ser
            100                 105                 110

Ile Val Ala Cys Val Lys Ala Ala Cys Glu Ala Lys Lys Lys Ala Thr
        115                 120                 125

Gly His Val Tyr Asp Ala Asn Lys Ile Val Tyr Thr Val Lys Val Glu
    130                 135                 140

Pro His Thr Gly Asp Tyr Val Ala Ala Asn Glu Thr His Ser Gly Arg
145                 150                 155                 160

Lys Thr Ala Ser Phe Thr Ile Ser Ser Glu Lys Thr Ile Leu Thr Met
                165                 170                 175

Gly Glu Tyr Gly Asp Val Ser Leu Leu Cys Arg Val Ala Ser Gly Val
            180                 185                 190
```

Asp Leu Ala Gln Thr Val Ile Leu Glu Leu Asp Lys Thr Val Glu His
            195                 200                 205

Leu Pro Thr Ala Trp Gln Val His Arg Asp Trp Phe Asn Asp Leu Ala
        210                 215                 220

Leu Pro Trp Lys His Glu Gly Ala Gln Asn Trp Asn Asn Ala Glu Arg
225                 230                 235                 240

Leu Val Glu Phe Gly Ala Pro His Ala Val Lys Met Asp Val Tyr Asn
                245                 250                 255

Leu Gly Asp Gln Thr Gly Val Leu Leu Lys Ala Leu Ala Gly Val Pro
            260                 265                 270

Val Ala His Ile Glu Gly Thr Lys Tyr His Leu Lys Ser Gly His Val
        275                 280                 285

Thr Cys Glu Val Gly Leu Glu Lys Leu Lys Met Lys Gly Leu Thr Tyr
    290                 295                 300

Thr Met Cys Asp Lys Thr Lys Phe Thr Trp Lys Arg Ala Pro Thr Asp
305                 310                 315                 320

Ser Gly His Asp Thr Val Val Met Glu Val Thr Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
        355                 360                 365

Gly Gly Phe Ile Glu Met Gln Leu Pro Pro Gly Asp Asn Ile Ile Tyr
    370                 375                 380

Val Gly Glu Leu Ser His Gln Trp Phe Gln Lys Gly Ser Ser Ile Gly
385                 390                 395                 400

Arg Val Phe Gln Lys Thr Lys Lys Gly Ile Glu Arg Leu Thr Val Ile
                405                 410                 415

Gly Glu His Ala Trp Asp Phe Gly Ser Ala Gly Gly Phe Leu Ser Ser
            420                 425                 430

Ile Gly Lys Ala Val His Thr Val Leu Gly Gly Ala Phe Asn Ser Ile
        435                 440                 445

Phe Gly Gly Val Gly Phe Leu Pro Lys Leu Leu Leu Gly Val Ala Leu
    450                 455                 460

Ala Trp Leu Gly Leu Asn Met Arg Asn Pro Thr Met Ser Met Ser Phe
465                 470                 475                 480

Leu Leu Ala Gly Gly Leu Val Leu Ala Met Thr Leu Gly Val Gly Ala
                485                 490                 495

<210> SEQ ID NO 62
<211> LENGTH: 493
<212> TYPE: PRT
<213> ORGANISM: Yellow fever virus

<400> SEQUENCE: 62

Ala His Cys Ile Gly Ile Thr Asp Arg Asp Phe Ile Glu Gly Val His
1               5                   10                  15

Gly Gly Thr Trp Val Ser Ala Thr Leu Glu Gln Asp Lys Cys Val Thr
            20                  25                  30

Val Met Ala Pro Asp Lys Pro Ser Leu Asp Ile Ser Leu Glu Thr Val
        35                  40                  45

Ala Ile Asp Arg Pro Ala Glu Val Arg Lys Val Cys Tyr Asn Ala Val
    50                  55                  60

Leu Thr His Val Lys Ile Asn Asp Lys Cys Pro Ser Thr Gly Glu Ala
65                  70                  75                  80

His Leu Ala Glu Glu Asn Glu Gly Asp Asn Ala Cys Lys Arg Thr Tyr
                85                  90                  95

Ser Asp Arg Gly Trp Gly Asn Gly Cys Gly Leu Phe Gly Lys Gly Ser
            100                 105                 110

Ile Val Ala Cys Ala Lys Phe Thr Cys Ala Lys Ser Met Ser Leu Phe
        115                 120                 125

Glu Val Asp Gln Thr Lys Ile Gln Tyr Val Ile Arg Ala Gln Leu His
    130                 135                 140

Val Gly Ala Lys Gln Glu Asn Trp Asn Thr Asp Ile Lys Thr Leu Lys
145                 150                 155                 160

Phe Asp Ala Leu Ser Gly Ser Gln Glu Val Glu Phe Ile Gly Tyr Gly
                165                 170                 175

Lys Ala Thr Leu Glu Cys Gln Val Gln Thr Ala Val Asp Phe Gly Asn
            180                 185                 190

Ser Tyr Ile Ala Glu Met Glu Thr Glu Ser Trp Ile Val Asp Arg Gln
        195                 200                 205

Trp Ala Gln Asp Leu Thr Leu Pro Trp Gln Ser Gly Ser Gly Gly Val
    210                 215                 220

Trp Arg Glu Met His His Leu Val Glu Phe Glu Pro Pro His Ala Ala
225                 230                 235                 240

Thr Ile Arg Val Leu Ala Leu Gly Asn Gln Glu Gly Ser Leu Lys Thr
                245                 250                 255

Ala Leu Thr Gly Ala Met Arg Val Thr Lys Asp Thr Asn Asp Asn Asn
            260                 265                 270

Leu Tyr Lys Leu His Gly Gly His Val Ser Cys Arg Val Lys Leu Ser
        275                 280                 285

Ala Leu Thr Leu Lys Gly Thr Ser Tyr Lys Ile Cys Thr Asp Lys Met
    290                 295                 300

Phe Phe Val Lys Asn Pro Thr Asp Thr Gly His Gly Thr Val Val Met
305                 310                 315                 320

Gln Val Lys Val Ser Lys Gly Ala Pro Cys Arg Ile Pro Val Ile Val
                325                 330                 335

Ala Asp Asp Leu Thr Ala Ala Ile Asn Lys Gly Ile Leu Val Thr Val
            340                 345                 350

Asn Pro Ile Ala Ser Thr Asn Asp Asp Glu Val Leu Ile Glu Val Asn
        355                 360                 365

Pro Pro Phe Gly Asp Ser Tyr Ile Ile Val Gly Arg Gly Asp Ser Arg
    370                 375                 380

Leu Thr Tyr Gln Trp His Lys Glu Gly Ser Ser Ile Gly Lys Leu Phe
385                 390                 395                 400

Thr Gln Thr Met Lys Gly Val Glu Arg Leu Ala Val Met Gly Asp Thr
                405                 410                 415

Ala Trp Asp Phe Ser Ser Ala Gly Gly Phe Phe Thr Ser Val Gly Lys
            420                 425                 430

Gly Ile His Thr Val Phe Gly Ser Ala Phe Gln Gly Leu Phe Gly Gly
        435                 440                 445

Leu Asn Trp Ile Thr Lys Val Ile Met Gly Ala Val Leu Ile Trp Val
    450                 455                 460

Gly Ile Asn Thr Arg Asn Met Thr Met Ser Met Ser Met Ile Leu Val
465                 470                 475                 480

Gly Val Ile Met Met Phe Leu Ser Leu Gly Val Gly Ala
                485                 490

-continued

```
<210> SEQ ID NO 63
<211> LENGTH: 501
<212> TYPE: PRT
<213> ORGANISM: West Nile virus

<400> SEQUENCE: 63

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Leu Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
        355                 360                 365

Ala Lys Val Leu Ile Glu Leu Glu Pro Pro Phe Gly Asp Ser Tyr Ile
    370                 375                 380

Val Val Gly Arg Gly Glu Gln Gln Ile Asn His His Trp His Lys Ser
```

-continued

```
            385                 390                 395                 400
Gly Ser Ser Ile Gly Lys Ala Phe Thr Thr Leu Lys Gly Ala Gln
                    405                 410                 415

Arg Leu Ala Ala Leu Gly Asp Thr Ala Trp Asp Phe Gly Ser Val Gly
            420                 425                 430

Gly Val Phe Thr Ser Val Gly Lys Ala Val His Gln Val Phe Gly Gly
                435                 440                 445

Ala Phe Arg Ser Leu Phe Gly Gly Met Ser Trp Ile Thr Gln Gly Leu
        450                 455                 460

Leu Gly Ala Leu Leu Leu Trp Met Gly Ile Asn Ala Arg Asp Arg Ser
465                 470                 475                 480

Ile Ala Leu Thr Phe Leu Ala Val Gly Gly Val Leu Leu Phe Leu Ser
                485                 490                 495

Val Asn Val His Ala
                500

<210> SEQ ID NO 64
<211> LENGTH: 495
<212> TYPE: PRT
<213> ORGANISM: Dengue-4 virus

<400> SEQUENCE: 64

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
                20                  25                  30

Thr Met Ala Gln Gly Lys Pro Thr Leu Asp Phe Glu Leu Thr Lys Thr
            35                  40                  45

Thr Ala Lys Glu Val Ala Leu Leu Arg Thr Tyr Cys Ile Glu Ala Ser
        50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
                100                 105                 110

Val Val Thr Cys Ala Lys Phe Ser Cys Ser Gly Lys Ile Thr Gly Asn
            115                 120                 125

Leu Val Gln Ile Glu Asn Leu Glu Tyr Thr Val Val Val Thr Val His
        130                 135                 140

Asn Gly Asp Thr His Ala Val Gly Asn Asp Thr Ser Asn His Gly Val
145                 150                 155                 160

Thr Ala Met Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
                180                 185                 190

Phe Asn Glu Met Ile Leu Met Lys Met Lys Lys Lys Thr Trp Leu Val
            195                 200                 205

His Lys Gln Trp Phe Leu Asp Leu Pro Leu Pro Trp Thr Ala Gly Ala
        210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
```

```
                        260                 265                 270
Gly Asp Gly Asn His Met Phe Ala Gly His Leu Lys Cys Lys Val Arg
                275                 280                 285
Met Glu Lys Leu Arg Ile Lys Gly Met Ser Tyr Thr Met Cys Ser Gly
            290                 295                 300
Lys Phe Ser Ile Asp Lys Glu Met Ala Glu Thr Gln His Gly Thr Thr
305                 310                 315                 320
Val Val Lys Val Lys Tyr Glu Gly Ala Gly Ala Pro Cys Lys Val Pro
                325                 330                 335
Ile Glu Ile Arg Asp Val Asn Lys Glu Lys Val Val Gly Arg Ile Ile
                340                 345                 350
Ser Ser Thr Pro Leu Ala Glu Asn Thr Asn Ser Val Thr Asn Ile Glu
                355                 360                 365
Leu Glu Pro Pro Phe Gly Asp Ser Tyr Ile Val Ile Gly Val Gly Asn
            370                 375                 380
Ser Ala Leu Thr Leu His Trp Phe Arg Lys Gly Ser Ser Ile Gly Lys
385                 390                 395                 400
Met Phe Glu Ser Thr Tyr Arg Gly Ala Lys Arg Met Ala Ile Leu Gly
                405                 410                 415
Glu Thr Ala Trp Asp Phe Gly Ser Val Gly Gly Leu Phe Thr Ser Leu
                420                 425                 430
Gly Lys Ala Val His Gln Val Phe Gly Ser Val Tyr Thr Thr Met Phe
            435                 440                 445
Gly Gly Val Ser Trp Met Ile Arg Ile Leu Ile Gly Phe Leu Val Leu
            450                 455                 460
Trp Ile Gly Thr Asn Ser Arg Asn Thr Ser Met Ala Met Thr Cys Ile
465                 470                 475                 480
Ala Val Gly Gly Ile Thr Leu Phe Leu Gly Phe Thr Val Gln Ala
                485                 490                 495

<210> SEQ ID NO 65
<211> LENGTH: 24
<212> TYPE: PRT
<213> ORGANISM: Influenza virus

<400> SEQUENCE: 65

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 66
<211> LENGTH: 7
<212> TYPE: PRT
<213> ORGANISM: Influenza virus

<400> SEQUENCE: 66

Trp Thr Gly Val Thr Gln Asn
1               5

<210> SEQ ID NO 67
<211> LENGTH: 18
<212> TYPE: PRT
<213> ORGANISM: Influenza virus

<400> SEQUENCE: 67

Ser Lys Ala Phe Ser Asn Cys Tyr Pro Tyr Asp Val Pro Asp Tyr Ala
1               5                   10                  15
```

Ser Leu

<210> SEQ ID NO 68
<211> LENGTH: 8
<212> TYPE: PRT
<213> ORGANISM: Influenza virus

<400> SEQUENCE: 68

Met Gly Leu Ile Tyr Asn Arg Met
1               5

<210> SEQ ID NO 69
<211> LENGTH: 9
<212> TYPE: PRT
<213> ORGANISM: Influenza virus

<400> SEQUENCE: 69

Thr Tyr Gln Arg Thr Arg Ala Leu Val
1               5

<210> SEQ ID NO 70
<211> LENGTH: 13
<212> TYPE: PRT
<213> ORGANISM: Influenza virus

<400> SEQUENCE: 70

Thr Tyr Gln Arg Thr Arg Thr Ala Leu Val Arg Thr Gly
1               5                   10

<210> SEQ ID NO 71
<211> LENGTH: 9
<212> TYPE: PRT
<213> ORGANISM: Influenza virus

<400> SEQUENCE: 71

Ser Ser Tyr Arg Arg Pro Val Gly Ile
1               5

<210> SEQ ID NO 72
<211> LENGTH: 9
<212> TYPE: PRT
<213> ORGANISM: Influenza virus

<400> SEQUENCE: 72

Ala Ser Asn Glu Asn Met Glu Thr Met
1               5

<210> SEQ ID NO 73
<211> LENGTH: 8
<212> TYPE: PRT
<213> ORGANISM: Influenza virus

<400> SEQUENCE: 73

Arg Thr Phe Ser Phe Gln Leu Ile
1               5

<210> SEQ ID NO 74
<211> LENGTH: 8
<212> TYPE: PRT
<213> ORGANISM: Influenza virus

<400> SEQUENCE: 74

Pro Asn Gly Tyr Ile Glu Gly Lys
1               5

-continued

```
<210> SEQ ID NO 75
<211> LENGTH: 9
<212> TYPE: PRT
<213> ORGANISM: Influenza virus

<400> SEQUENCE: 75

Val Thr Gly Leu Arg Asn Ile Pro Ser
1               5

<210> SEQ ID NO 76
<211> LENGTH: 15
<212> TYPE: PRT
<213> ORGANISM: Influenza virus

<400> SEQUENCE: 76

Ala Leu Asn Asn Arg Phe Gln Ile Lys Gly Val Glu Leu Lys Ser
1               5                   10                  15
```

FLAVIVIRUS VACCINE VECTOR AGAINST INFLUENZA VIRUS

CROSS-REFERENCE TO RELATED APPLICATIONS

This application claims priority under 35 U.S.C. §371 from international application PCT/US2008/001309, filed Jan. 31, 2008, which claims benefit of U.S. Provisional Patent Application No. 60/898,651, filed Jan. 31, 2007.

FIELD OF THE INVENTION

This invention relates to viral vectors and methods employing these vectors.

BACKGROUND OF THE INVENTION

Vaccination is one of the greatest achievements of medicine, and has spared millions of people the effects of devastating diseases. Before vaccines became widely used, infectious diseases killed thousands of children and adults each year in the United States alone, and so many more worldwide. Vaccination is widely used to prevent and treat infection by bacteria, viruses, and other pathogens, and also is an approach that is used in the prevention and treatment of cancer. Several different approaches are used in vaccination, including the administration of live-attenuated pathogen, killed pathogen, and inactive pathogen subunits. In the case of viral infection, live vaccines have been found to confer the most potent and durable protective immune responses.

Live-attenuated vaccines have been developed against flaviviruses, which are small, enveloped, positive-strand RNA viruses that are generally transmitted by infected mosquitoes and ticks. The *Flavivirus* genus of the Flaviviridae family includes approximately 70 viruses, many of which, such as yellow fever (YF), dengue (DEN), Japanese encephalitis (JE), and tick-borne encephalitis (TBE) viruses, are major human pathogens (rev. in Burke and Monath, Fields Virology, 4$^{th}$ Ed., p. 1043-1126, 2001).

Different approaches have been used in the development of vaccines against flaviviruses. In the case of yellow fever virus, for example, two vaccines (yellow fever 17D and the French neurotropic vaccine) were developed by serial passage (Monath, "Yellow Fever," In Plotkin and Orenstein, Vaccines, 3$^{rd}$ ed., Saunders, Philadelphia, pp. 815-879, 1999). Another approach to attenuation of flaviviruses for use in vaccination involves the construction of chimeric flaviviruses, which include components of two (or more) different flaviviruses. Understanding how such chimeras are constructed requires an explanation of flavivirus structure.

*Flavivirus* proteins are produced by translation of a single, long open reading frame to generate a polyprotein, which is followed by a complex series of post-translational proteolytic cleavages of the polyprotein by a combination of host and viral proteases to generate mature viral proteins (Amberg et al., J. Virol. 73:8083-8094, 1999; Rice, "Flaviviridae," In *Virology*, Fields (ed.), Raven-Lippincott, New York, 1995, Volume I, p. 937). The virus structural proteins are arranged in the polyprotein in the order C-prM-E, where "C" is capsid, "prM" is a precursor of the viral envelope-bound M protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polyprotein.

Chimeric flaviviruses have been made that include structural and non-structural proteins from different flaviviruses. For example, the so-called CHIMERIVAX™ (a first flavivirus (i.e., a backbone flavivirus) in which a structural protein (or proteins) has been replaced with a corresponding structural protein (or proteins) of a second virus) technology employs the yellow fever 17D virus capsid and nonstructural proteins to deliver the envelope proteins (M and E) of other flaviviruses (see, e.g., Chambers et al., J. Virol. 73:3095-3101, 1999). This technology has been used to develop vaccine candidates against dengue, Japanese encephalitis (JE), West Nile (WN), and St. Louis encephalitis (SLE) viruses (see, e.g., Pugachev et al., in New Generation Vaccines, 3$^{rd}$ ed., Levine et al., eds., Marcel Dekker, New York, Basel, pp. 559-571, 2004; Chambers et al., J. Virol. 73:3095-3101, 1999; Guirakhoo et al., Virology 257:363-372, 1999; Monath et al., Vaccine 17:1869-1882, 1999; Guirakhoo et al., J. Virol. 74:5477-5485, 2000; Arroyo et al., Trends Mol. Med. 7:350-354, 2001; Guirakhoo et al., J. Virol. 78:4761-4775, 2004; Guirakhoo et al., J. Virol. 78:9998-10008, 2004; Monath et al., J. Infect. Dis. 188:1213-1230, 2003; Arroyo et al., J. Virol. 78:12497-12507, 2004; and Pugachev et al., Am. J. Trop. Med. Hyg. 71:639-645, 2004).

CHIMERIVAX™ (a first flavivirus (i.e., a backbone flavivirus) in which a structural protein (or proteins) has been replaced with a corresponding structural protein (or proteins) of a second virus)-based vaccines have been shown to have favorable properties with respect to properties such as replication in substrate cells, low neurovirulence in murine models, high attenuation in monkey models, high genetic and phenotypic stability in vitro and in vivo, inefficient replication in mosquitoes (which is important to prevent uncontrolled spread in nature), and the induction of robust protective immunity in mice, monkeys, and humans following administration of a single dose, without serious post-immunization side effects. Indeed, the CHIMERIVAX™ (a first flavivirus (i.e., a backbone flavivirus) in which a structural protein (or proteins) has been replaced with a corresponding structural protein (or proteins) of a second virus)-JE vaccine virus, containing the prM-E genes from the SA14-14-2 JE virus (live attenuated JE vaccine used in China), was successfully tested in preclinical and Phase I and II clinical trials (Monath et al., Vaccine 20:1004-1018, 2002; Monath et al., J. Infect. Dis. 188:1213-1230, 2003). Similarly, successful Phase I clinical trials have been conducted with a CHIMERIVAX™ (a first flavivirus (i.e., a backbone flavivirus) in which a structural protein (or proteins) has been replaced with a corresponding structural protein (or proteins) of a second virus)-WN vaccine candidate, which contains prM-E sequences from a West Nile virus (NY99 strain), with three specific amino acid changes incorporated into the E protein to increase attenuation (Arroyo et al., J. Virol. 78:12497-12507, 2004).

In addition to being used as vaccines against flavivirus infection, flaviviruses, such as chimeric flaviviruses, have been proposed for use as vectors for the delivery of other, non-flavivirus peptides. In one example of such a use, a rational approach for insertion of foreign peptides into the envelope protein of YF17D virus was described, based on knowledge of the tertiary structure of the flavivirus particle, as resolved by cryoelectron microscopy and fitting the known X-ray structure of the protein dimer into an electron density map (Rey et al., Nature 375:291-298, 1995; Kuhn et al., Cell 108:717-725, 2002). The three-dimensional structure of the protein trimer in its post-fusion conformation has also been resolved (Modis et al., Nature 427:313-319, 2004; Bressanelli et al., EMBO J. 23:728-738, 2004). Galler and co-workers examined the three-dimensional structures of the envelope protein dimer and trimer and concluded that the fg loop of dimerization domain II should be solvent-exposed in both the dimer and trimer conformations. They used this loop to insert malaria humoral and T-cell epitopes into the envelope protein of YF17D virus and recovered a few viable mutants (Bonaldo et al., J. Virol. 79:8602-8613, 2005; Bonaldo et al., J. Mol. Biol. 315:873-885, 2002; WO 02/072835). Use of this approach, however, does not ensure that a selected site is permissive/optimal for the insertion of every desired foreign peptide in terms of efficient virus replication (as evidenced by some of the Galler et al. data), immunogenicity, and stability. Further, this approach is not applicable to viral proteins for which three-dimensional structures are unknown (e.g., prM/M, NS1, and most other NS proteins of flaviviruses).

In another approach, the envelope protein of CHI-MERIVAX™ (a first flavivirus (i.e., a backbone flavivirus) in which a structural protein (or proteins) has been replaced with a corresponding structural protein (or proteins) of a second virus)-JE was probed for permissive insertion sites using a transposon. According to this approach, an inserted transposon in a viable mutant virus is replaced with a desired foreign peptide (see, e.g., WO 02/102828). In yet another approach, foreign sequences were inserted into the yellow fever virus strain YF-17D, downstream of the polyprotein open reading frame (US 2004/0241821).

SUMMARY OF THE INVENTION

The invention provides flaviviruses that include one or more insertions of sequences encoding a heterologous peptide or protein between (i) nucleotides encoding amino acids corresponding to amino acids 277 and 278 of the envelope protein of Japanese encephalitis virus, (ii) nucleotides encoding amino acids corresponding to amino acids 207 and 208 of the envelope protein of Japanese encephalitis virus, or (iii) nucleotides encoding amino acids within five amino acids of those corresponding to amino acids 277 and 278, or amino acids 207 and 208, of the envelope protein of Japanese encephalitis virus.

By amino acids "corresponding to" the indicated Japanese encephalitis amino acids is meant, in addition to the indicated amino acids of Japanese encephalitis virus, amino acids in envelope proteins of other flaviviruses that align with these or closely positioned amino acids, as can readily be determined by those of skill in the art (see, e.g., below and FIG. 1).

The flaviviruses of the invention can be chimeric flaviviruses, including structural proteins of a first flavivirus and non-structural proteins of a second flavivirus (e.g., a yellow fever virus, such as YF17D (also see below). For example, the flaviviruses can include pre-membrane and envelope proteins of the first flavivirus and capsid and non-structural proteins of the second flavivirus.

Examples of first flaviviruses that can be included in the chimeric flaviviruses of the invention include Japanese encephalitis, Dengue-1, Dengue-2, Dengue-3, Dengue-4, Murray Valley encephalitis, St. Louis encephalitis, West Nile, Kunjin, Rocio encephalitis, Ilheus, Tick-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

The heterologous peptides or proteins encoded by heterologous sequences of the flaviviruses of the invention can be, e.g., vaccine antigens. Such vaccine antigens can be derived from an infectious agent, such as an influenza virus. Examples of such vaccine antigens include hemagglutinin, neuraminidase, M2, and immunogenic fragments thereof (e.g., the M2e region of the M2 protein or a fragment thereof, such as peptides of the sequences MSLLTEVETPIR (SEQ ID NO:1) or MSLLTEVETPIRNEWGSRSNDSSD (SEQ ID NO:2)), which may also include amino and/or carboxy terminal glycine linker sequences (e.g., 1 or 2 glycines on either or both ends). In other examples, the heterologous peptide or protein is present between nucleotides encoding amino acids corresponding to amino acids 277 and 278 of the envelope protein of Japanese encephalitis virus, and/or the heterologous peptide or protein is present between nucleotides encoding amino acids corresponding to amino acids 207 and 208 of the envelope protein of Japanese encephalitis virus. Specific examples of inserted sequences that can be used in the invention include those selected from the group consisting of: SEQ ID NOs:1, 2, 13-15, 20-59, and 65-76.

Further, the flaviviruses of the invention may optionally include a deletion of 3'-untranslated region and/or the NS1 sequences, as described further below.

The invention also includes methods of administering protein and/or peptides to subjects, which involve administration of the flaviviruses described above or elsewhere herein.

Also featured in the invention are nucleic acid molecules encoding the flaviviruses described above or elsewhere herein, as well as pharmaceutical compositions including such flaviviruses.

The invention also includes methods of producing flaviviruses such as those described above and elsewhere herein, which involve culturing cells into which RNA corresponding to the viruses has been introduced at a temperature below 37° C. (e.g., 30° C.-36° C. or 34° C.). Further, the invention includes methods of propagating the flaviviruses, which involve incubating cells infected with the viruses at a temperature below 37° C. (e.g., 30° C.-36° C. or 34° C.).

Also included in the invention are flavivirus replicons including one or more insertions of sequences encoding a heterologous peptide or protein between (i) nucleotides encoding amino acids corresponding to amino acids 277 and 278 of the envelope protein of Japanese encephalitis virus, (ii) nucleotides encoding amino acids corresponding to amino acids 207 and 208 of the envelope protein of Japanese encephalitis virus, or (iii) nucleotides encoding amino acids within five amino acids of those corresponding to amino acids 277 and 278, or amino acids 207 and 208, of the envelope protein of Japanese encephalitis virus. Corresponding pharmaceutical compositions, as well as therapeutic and prophylactic methods, are also included in the invention.

The invention provides several advantages. For example, the live, attenuated viral vectors of the invention induce strong, long-lasting immune responses against specific antigens. The vectors of the invention can be used to confer immunity to infectious diseases, such as influenza, or to disease-related proteins such as cancer antigens and the like. As an example, the invention can be used to deliver influenza virus M2e (or a fragment thereof), which is the external portion of M2, a minor influenza A surface protein that is conserved among diverse influenza viruses and may serve as the basis for a vaccine that protects against all influenza A strains (Neirynck et al., Nat. Med. 5(10):1157-1163, 1999; Fiers et al., Virus Res. 103(1-2):173-176, 2004).

An additional advantage of the vectors of the invention is that, as described further below, they can be used to deliver relatively large antigens, as compared to many previously known viral vectors. Thus, as an example, in addition to M2e, the vectors of the invention can advantageously be used to administer larger portions of M2 or even full length M2.

The advantages of using live vectors, such as the flavivirus-based vectors of the invention, also include (i) expansion of the antigenic mass following vaccine inoculation; (ii) the lack of need for an adjuvant; (iii) the intense stimulation of innate and adaptive immune responses (YF17D, for example, is the most powerful known immunogen); (iv) the possibility of more favorable antigen presentation due to, e.g., the ability of CHIMERIVAX™ (a first flavivirus (i.e., a backbone flavivirus) in which a structural protein (or proteins) has been replaced with a corresponding structural protein (or proteins) of a second virus) (derived from YF17D) to infect antigen presenting cells, such as dendritic cells and macrophages; (v) the possibility to obtain a single-dose vaccine providing lifelong immunity; (vi) the envelopes of CHIMERIVAX™ (a first flavivirus (i.e., a backbone flavivirus) in which a structural protein (or proteins) has been replaced with a corresponding structural protein (or proteins) of a second virus) vaccine viruses are easily exchangeable, giving a choice of different recombinant vaccines, some of which are more appropriate than the others in different geographic areas or for sequential use; (vii) the possibility of modifying complete live flavivirus vectors into packaged, single-round-replication replicons, in order to eliminate the chance of adverse events or to minimize the effect of anti-vector immunity during sequential use; and (viii) the low cost of manufacture.

Additional advantages provided by the invention relate to the fact that chimeric flavivirus vectors of the invention are sufficiently attenuated so as to be safe, and yet are able to induce protective immunity to the flaviviruses from which the proteins in the chimeras are derived and, in particular, the proteins or peptides inserted into the chimeras. Additional safety comes from the fact that some of the vectors used in the invention are chimeric, thus eliminating the possibility of reversion to wild type. An additional advantage of the vectors of the invention is that flaviviruses replicate in the cytoplasm of cells, so that the virus replication strategy does not involve integration of the viral genome into the host cell, providing an important safety measure. Further, a single vector of the invention can be used to deliver multiple epitopes from a single antigen, or epitopes derived from more than one antigen.

An additional advantage provided by the invention relates to the use of new growth conditions for propagating viral vectors, such as those described herein. As is discussed further below, these conditions enable the production of relatively high titer virus, with increased immunogenicity.

Other features and advantages of the invention will be apparent from the following detailed description, the drawings, and the claims.

BRIEF DESCRIPTION OF THE DRAWINGS

FIG. 1 is a schematic representation of a JE envelope glycoprotein 3D model showing two amino acid positions on tips of surface exposed loops potentially favoring M2e insertion. Below is a multiple sequence alignment of several representative Flavivirus members for sequences around the identified sites, confirming the structural plasticity of these E protein regions (SEQ ID NOs:3-12). Modeling of the 3D structure of JEV envelope (NP 775666 (SEQ ID NO:60)) was based on the WNV E protein (2HGO) template using Swissmodel prediction algorithm, and PDBViewer v.3.7 and Pov-Ray software (expasy.com). Boxed are fg and kl loops of E protein, and Gly207 and Ser277 side chains are shown. Multiple alignment was performed using ClustalW2 software (http://ebi.ac.uk/Tools/clustalw2/index.html) and amino acid sequences of flaviviruses derived from PubMed (TBEV: NP 775503 (SEQ ID NO:61); YFV: NP 740305 (SEQ ID NO:62); WNV: YP 001527880 (SEQ ID NO:63); DEN4: NP 740317 (SEQ ID NO:64)). M2e insert sequences with glycine linkers are also shown (SEQ ID NOs:13-15).

FIG. 5 is an illustration of the stability of an M2e insert between amino acids 277 and 288 of the E protein after 10 passages in Vero cells at low MOI. Heterogenic uncloned E277M2e virus was twice plaque purified and a large plaque phenotype clone was selected and amplified twice on Vero cells to produce E277M2e-P2 virus (titer $1.05 \times 10^6$ PFU/ml) used in all following experiments. Purified E277M2e-P2 virus had homogeneous plaques, all found M2e positive when stained with Mab 14C2 in immunofocus assay (A). E277M2e-P2 virus has undergone 10 passages on Vero cells at low 0.001 MOI to produce E277M2e-P12 virus. The latter was shown to be stably expressing an M2e insert, as confirmed by immunostaining with Mab 14C2 (B).

FIG. 8 is a set of images and a table showing that E277M2e-P2 virus can be effectively neutralized by M2 specific antibodies, such as Mab 14C2 or polyclonal anti-M2 antibodies. This provides evidence that the M2e insert is expressed on the surface of the E protein, and present in such a conformation on the surface of CVJE virions that makes it accessible for recognition by antibodies. Standard $PRNT_{50}$ combined with immunofocus staining assays were performed using 4-fold dilutions of Mab 14C2 (initial concentration 1 µg/µl) to neutralize CVJE (A) or E277M2e-M2 (B). Approximate neutralization titers for Mab 14C2 and a polyclonal antibody raised against HBc-M2e particles (Acam-FluA) vaccine against CVJE and E277M2e-P2 are presented in (C).

FIG. 9 is a set of graphs showing humoral anti-M2e immune responses in mice immunized with E277M2e-P2 or CVJE parent viruses and Acam-FluA vaccine. Female Balb/C 4 week-old mice in groups of 10 were IP immunized and boosted on day 30 after prime with either 7 $\log_{10}$ PFU of CVJE, $\log_{10}$ PFU of E277M2e-P2, or 10 µg of Acam-FluA adjuvanted with Alhydrogel™. On day 60 after prime, mice were bled and titers of total IgG as well as IgG1, IgG2a, IgG2b, and IgG3 isotypes in serum were determined by end point ELISA against M2e peptide antigen.

DETAILED DESCRIPTION

Figure 2A:
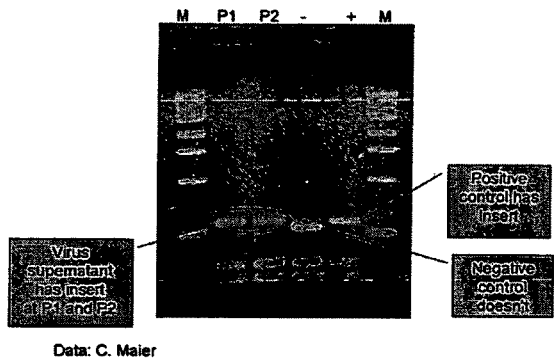
FIG. 2A is an image showing the results of RT-PCR analysis of culture supernatants containing CV-JE in which an M2e peptide was inserted at position 278 of the E protein (ES275: M2e). The insert is detected as a higher molecular weight band (digested PCR product).

The invention provides live, attenuated viral vectors that can be used in the administration of vaccine antigens, such as vaccine antigens against influenza virus. Also included in the invention are methods of using these vectors in methods for preventing and treating influenza virus infection, pharmaceutical compositions including the vectors, and nucleic acid molecules corresponding to genomes of the viral vectors or the complements thereof. As discussed further below, the viral vaccine vectors of the invention can be used to induce long-lasting immune responses against specific influenza antigens. For example, the vaccine vectors of the present invention can be used to express a universal influenza antigen that is inserted into a highly immunogenic site, the flavivirus envelope (E) protein. The invention provides compositions intended to protect animals, including humans, against a broad range of influenza strains. Further, the invention provides methods of making and propagating viral vectors such as those of the invention. The vectors, methods, and compositions of the invention are described further, as follows.

Viral Vectors

In certain examples, the vectors of the invention are based on CHIMERIVAX™ (a first flavivirus (i.e., a backbone flavivirus) in which a structural protein (or proteins) has been replaced with a corresponding structural protein (or proteins) of a second virus) viruses, which, as described above, consist of a first flavivirus (i.e., a backbone flavivirus) in which a structural protein (or proteins) has been replaced with a corresponding structural protein (or proteins) of a second virus. For example, the chimeras can consist of a first flavivirus in which the prM and E proteins have been replaced with the prM and E proteins of a second flavivirus. As is discussed above, flavivirus proteins, including those of the chimeric flaviviruses described herein, are produced as a polyprotein that is post-translationally cleaved into subunit proteins: the amino terminal structural proteins, capsid (C), pre-membrane (prM), and envelope (E), and the carboxyl terminal non-structural proteins, NS1, NS2A, NS2B, NS3, NS4A, NS4B, and NS5.

As is described further below, the vectors of the invention include insertions of influenza virus sequences, such as influenza virus M2e sequences. Three specific examples of such vectors, which are based on chimeric yellow fever/Japanese encephalitis viruses, are described below. In these vectors, influenza sequences, such as M2e sequences, are inserted between Japanese encephalitis virus envelope amino acids 277 and 278 ($E_{S275:M2e}$ and E277M2e viruses) or (ii) between amino acids 207 and 208 sequence ($E_{G202:M2e}$ virus). The inserts in these examples have the following amino acid sequences: (i) $(G)_{1-2}$MSLLTEVETPIRGG (SEQ ID NOs:13 or 15), comprising an N-terminal one- or two-glycine linker, followed by the first 12 amino acids of influenza protein M2, followed in turn by a C-terminal two-glycine linker, and (i) GGMSLLTEVETPIRNEWGSRSNDSSDGG (SEQ ID NO:14), comprising first 24 amino acids of influenza M2 protein flanked from both terminus by two-glycine linkers. Additional details concerning these examples are provided below.

In addition to positions corresponding to those of Japanese encephalitis virus between amino acids 277 and 278, and amino acids 207 and 208, the invention also includes vectors in which inserts are made at different sites in these areas. Thus, for example, the vectors can include insertions between the following pairs of amino acids: 272/273, 273/274, 274/275, 275/276, 276/277, 278/279, 279/280, 280/281, 281/282, 282/283; 202/203, 203/204, 204/205, 205/206, 206/207, 208/209, 209/210, 210/211, 211/212, and 212/213.

In the case of non-JE sequences, the insertions can be made, for example, between amino acids 203 and 204 or amino acids 280 and 281 of Tick-borne encephalitis virus; between amino acids 199 and 200 or amino acids 273 and 274 of yellow fever virus; between amino acids 207 and 208 or amino acids 278 and 279 of West Nile virus; and between amino acids 202 and 203 or amino acids 275 and 276 of Dengue-4 virus. Similar to JE, as discussed above, the invention includes vectors in which insertions are made in non-JE sequences within 5 amino acids of the sites corresponding to the JE insertion sites, as noted above.

The chimeric viruses that are used in the invention can be made from any combination of flaviviruses. As is noted above, the chimeras can include structural proteins from a first flavivirus (pre-membrane (prM), envelope (E), and/or capsid (C)) and non-structural proteins from a second, different flavivirus (or flavivirus serotype). For example, the chimeras can include pre-membrane and envelope proteins from a first flavivirus and capsid and non-structural proteins from a second flavivirus.

Specific examples of chimeras that can be used in the invention include yellow fever virus capsid and non-structural sequences, and Japanese encephalitis virus pre-membrane and envelope sequences. However, other viruses can be used as well. Examples of particular flaviviruses that can be used in the invention, as first or second viruses, include mosquito-borne flaviviruses, such as Japanese encephalitis, Dengue (serotypes 1-4), yellow fever, Murray Valley encephalitis, St. Louis encephalitis, West Nile, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses; as well as viruses from the Hepacivirus genus (e.g., Hepatitis C virus).

Details of making chimeric viruses that can be used in the invention are provided, for example, in U.S. Pat. Nos. 6,962,708 and 6,696,281; PCT international applications WO 98/37911 and WO 01/39802; and Chambers et al., J. Virol. 73:3095-3101, 1999, the contents of each of which are incorporated by reference herein in its entirety. In addition, these chimeric viruses can include attenuating mutations, such as those described in the following documents, the contents of each of which is incorporated herein by reference: WO 2003/103571; WO 2005/082020; WO 2004/045529; WO 2006/044857; PCT/US2006/015241; U.S. Pat. No. 6,685,948 B1; U.S. Patent Application Publication US 2004/0052818 A1; U.S. Patent Application Publication 2005/0010043 A1; WO 02/074963; WO 02/095075 A1; WO 03/059384 A1; WO 03/092592 A2; as well as the documents cited above.

A specific example of a type of chimeric virus that can be used in the invention is the human yellow fever virus vaccine strain, YF17D, in which the prM and E proteins have been replaced with prM and E proteins of another flavivirus, such as Japanese encephalitis virus, West Nile virus, St. Louis encephalitis virus, Murray Valley encephalitis virus, a Dengue virus, or any other flavivirus, such as one of those listed above. For example, the following chimeric flaviviruses, which were deposited with the American Type Culture Collection (ATCC) in Manassas, Va., U.S.A. under the terms of the Budapest Treaty and granted a deposit date of Jan. 6, 1998, can be used in the invention: Chimeric Yellow Fever 17D/Japanese Encephalitis SA14-14-2 Virus (YF/JE A1.3; ATCC accession number ATCC VR-2594) and Chimeric Yellow Fever 17D/Dengue Type 2 Virus (YF/DEN-2; ATCC accession number ATCC VR-2593).

Among the advantages of using the CHIMERIVAX™ (a first flavivirus (i.e., a backbone flavivirus) in which a structural protein (or proteins) has been replaced with a corresponding structural protein (or proteins) of a second virus) vaccines as vectors, a main advantage is that the envelope proteins (which are the main antigenic determinants of immunity against flaviviruses, and in this case, anti-vector immunity) can be easily exchanged allowing for the construction of several different vaccines using the same YF17D backbone that can be applied sequentially to the same individual. In addition, different recombinant CHIMERIVAX™ (a first flavivirus (i.e., a backbone flavivirus) in which a structural protein (or proteins) has been replaced with a corresponding structural protein (or proteins) of a second virus) insertion vaccines can be determined to be more appropriate for use in specific geographical regions in which different flaviviruses are endemic, as dual vaccines against an endemic flavivirus and another targeted pathogen. For example, CHIMERIVAX™ (a first flavivirus (i.e., a backbone flavivirus) in which a structural protein (or proteins) has been replaced with a corresponding structural protein (or proteins) of a second virus)-JE-influenza vaccine may be more appropriate in Asia, where JE is endemic, to protect from both JE and influenza, YF17D-influenza vaccine may be more appropriate in Africa and South America, where YF is endemic, CHIMERIVAX™ (a first flavivirus (i.e., a backbone flavivirus) in which a structural protein (or proteins) has been replaced with a corresponding structural protein (or proteins) of a second virus)-WN-influenza may be more appropriate for the U.S. and parts of Europe and the Middle East, in which WN virus is endemic, and CHIMERIVAX™ (a first flavivirus (i.e., a backbone flavivirus) in which a structural protein (or proteins) has been replaced with a corresponding structural protein (or proteins) of a second virus)-Dengue-influenza-may be more appropriate throughout the tropics where dengue viruses are present.

In addition to chimeric flaviviruses, other flaviviruses, such as non-chimeric flaviviruses, can be used as vectors according to the present invention. Examples of such viruses that can be used in the invention include live, attenuated vaccines, such as those derived from the YF17D strain, which was originally obtained by attenuation of the wild-type Asibi strain (Smithburn et al., "Yellow Fever Vaccination," World Health Organization, p. 238, 1956; Freestone, in Plotkin et al. (eds.), Vaccines, $2^{nd}$ edition, W.B. Saunders, Philadelphia, U.S.A., 1995). An example of a YF17D strain from which viruses that can be used in the invention can be derived is YF17D-204 (YF-VAX®, Sanofi-Pasteur, Swiftwater, Pa., USA; Stamaril®, Sanofi-Pasteur, Marcy-L'Etoile, France; ARILVAX™, Chiron, Speke, Liverpool, UK; FLAVIMUN®, Berna Biotech, Bern, Switzerland; YF17D-204 France (X15067, X15062); YF17D-204, 234 US (Rice et al., Science 229:726-733, 1985)), while other examples of such strains that can be used are the closely related YF17DD strain (GenBank Accession No. U 17066), YF17D-213 (GenBank Accession No. U17067), and yellow fever virus 17DD strains described by Caller et al., Vaccines 16(9/10):1024-1028, 1998. In addition to these strains, any other yellow fever virus vaccine strains found to be acceptably attenuated in humans, such as human patients, can be used in the invention.

Further, in addition to live viruses, as discussed above, packaged replicons expressing foreign proteins or peptides can be used in the invention. This approach can be used, for example, in cases in which it may be desirable to increase safety or to minimize antivector immunity (neutralizing antibody response against the envelope proteins), in order to use the same vector for making different vaccines that can be applied to the same individual. Technology for the construction of single-round replicons is well established, and the immunogenic potential of replicons has been demonstrated (Jones et al., Virology 331:247-259, 2005; Molenkamp et al., J. Virol. 77:1644-1648, 2003; Westaway et al., Adv. Virus. Res. 59:99-140, 2003). In an example of such a replicon, most of the prM and E envelope protein genes are deleted. Therefore, it can replicate inside cells, but cannot generate virus progeny (hence single-round replication). It can be packaged into viral particles when the prM-E genes are provided in trans. Still, when cells are infected by such packaged replicon (e.g., following vaccination), a single round of replication follows, without further spread to surrounding cell/tissues.

Protective epitopes from different pathogens can be combined in one virus, resulting in triple-, quadruple-, etc., vaccines. Also, a CHIMERIVAX™ (a first flavivirus (i.e., a backbone flavivirus) in which a structural protein (or proteins) has been replaced with a corresponding structural protein (or Proteins) of a second virus) variant containing the envelope from a non-endemic flavivirus can be used to avoid the risk of natural antivector immunity in a population that otherwise could limit the effectiveness of vaccination in a certain geographical area (e.g., CHIMERIVAX™ (a first flavivirus (i.e., a backbone flavivirus) in which a structural protein (or proteins) has been replaced with a corresponding structural protein (or proteins) of a second virus)-JE vector may be used in the U.S. where JE is not present).

Heterologous Proteins and Peptides

The vectors of the invention can be used to deliver or produce any peptide or protein of prophylactic, therapeutic, diagnostic, or experimental interest. For example, the vectors can be used in the induction of an immune response (prophylactic or therapeutic) against any protein-based antigen that is inserted in the envelope protein (e.g., between amino acids 277 and 278 of the E protein, or between amino acids 207 and 208, as described above and elsewhere herein. In some cases, it may be desirable to maintain the size of the flavivirus into which an insert gene is introduced, as much as possible, in order to maintain virus genetic stability and viability. This can be achieved, for example, by the deletion of sequences in the 3'-untranslated region of the virus (see below and also U.S. Pat. No. 6,685,948; US 2005/0010043 A1; PCT/US2006/015241; WO 02/074963; WO 02/095075 A1; WO 03/059384 A1; and WO 03/092592 A2; also see Deubel et al., "Biological and Molecular Variations of Yellow Fever Virus Strains," In Saluzzo et al. (eds.), "Factors in the Emergence of Arbovirus Diseases" Elsevier, Paris, 1997, pages 157-165).

In another example, portions of the NS1 gene (e.g., all or most of the NS1 gene) can be deleted to accommodate an insert. The elimination of NS1 (ΔNS1), which is about 1.2 kb in length, allows the insertion of transgenes similar in size. A consequence of this deletion is that the NS1 function must now be supplied in trans by introduction of the NS1 gene into the cell line used to produce a ΔNS 1 chimera (see, e.g., Lindenbach et al., J. Virol. 71:9608-9617, 1997). The chimeric viral particles produced in this way can infect cells, but are not capable of replication in vivo. This creates an antigen gene-delivery vector, which, in addition to avoiding potential problems with genome size limitations, has different properties from the replication-competent chimeras described above (e.g., decreased virulence).

Antigens that can be used in the invention can be derived from, for example, infectious agents such as viruses, bacteria, and parasites. A specific example of such an infectious agent is influenza viruses, including those that infect humans (e.g., A (e.g., strain A/HK/8/68), B, and C strains), as well as avian influenza viruses. A specific example of an epitope that can be included in the vectors of the invention is the M2e epitope of influenza A (strain A/HK/8/68). One example of such an epitope consists of an insert has the following amino acid sequence: $(G)_{1-2}$MSLLTEVETPIRGG (SEQ ID NOs:13 or 15), comprising an N-terminal one- or two-glycine linker, followed by the first 12 amino acids of influenza protein M2, followed in turn by a C-terminal two-glycine linker.

Other examples of antigens from influenza viruses include those derived from hemagglutinin (HA; e.g., any one of H1-H16, or subunits thereof) (or HA subunits HA1 and HA2), neuraminidase (NA; e.g., any one of N1-N9), M2 (e.g., M2e), M1, nucleoprotein (NP), and B proteins. For example, peptides including the hemagglutinin precursor protein cleavage site (HA0) (e.g., NIPSIQSRGLFGAIAGFIE (SEQ ID NO:20) for A/H1 strains, NVPEKQTRGIFGAIAGFIE (SEQ ID NO:21) for A/H3 strains, and PAKLLKERGFFGAIAGFLE (SEQ ID NO:22) for influenza B strains), or HA peptide SKAFSNCYPYDVPDYASL (SEQ ID NO:23), or its variant SKAFSNSYPYDVPDYASL (SEQ ID NO:24), or M2e (e.g., MSLLTEVETPIRNEWGSRSNDSSD (SEQ ID NO:2); also see European Patent No. 0 996 717 B1, the contents of which are incorporated herein by reference), as well as peptide sequences listed in supplementary table 10 of Bui et al., Proc. Natl. Acad. Sci. U.S.A. 104:246-251, 2007, can be used (SEQ ID NOs:65-76). Other examples of peptides that are conserved in influenza can be used in the invention and include: NBe peptide conserved for influenza B (e.g., consensus sequence MNNATFNYTNVNPISHIRGS (SEQ ID NO:25)); the extracellular domain of BM2 protein of influenza B (e.g., consensus MLEPFQ (SEQ ID NO:26)); and the M2e peptide from the H5N1 avian flu (e.g., MSLLTE-VETLTRNGWGCRCSDSSD (SEQ ID NO:27)). Use of influenza virus M2 (or fragments thereof, such as M2e) is particularly advantageous, because the sequence of this protein is highly conserved, as compared with the sequences of other influenza proteins (see, e.g., European Patent 0 996 717 B1).

Further examples of influenza proteins and peptides that can be used in the invention, as well as proteins from which such peptides can be derived (e.g., by fragmentation) are described in US 2002/0165176, US 2003/0175290, US 2004/0055024, US 2004/0116664, US 2004/0219170, US 2004/0223976, US 2005/0042229, US 2005/0003349, US 2005/0009008, US 2005/0186621, U.S. Pat. No. 4,752,473, U.S. Pat. No. 5,374,717, U.S. Pat. No. 6,169,175, U.S. Pat. No. 6,720,409, U.S. Pat. No. 6,750,325, U.S. Pat. No. 6,872,395, WO 93/15763, WO 94/06468, WO 94/17826, WO 96/10631, WO 99/07839, WO 99/58658, WO 02/14478, WO 2003/102165, WO 2004/053091, WO 2005/055957, and Tables 1-4 (and references cited therein), the contents of which are incorporated by reference.

Protective epitopes from other human/veterinary pathogens, such as parasites (e.g., malaria), other pathogenic viruses (e.g., human papilloma virus (HPV), herpes simplex viruses (HSV), human immunodeficiency viruses (HIV), and hepatitis C viruses (HCV)), and bacteria (e.g., *Mycobacterium tuberculosis, Clostridium difficile*, and *Helicobacter pylori*) can also be included in the vectors of the invention. Examples of additional pathogens, as well as antigens and epitopes from these pathogens, which can be used in the invention are provided in WO 2004/053091, WO 03/102165, WO 02/14478, and US 2003/0185854, the contents of which are incorporated herein by reference. Further, additional therapeutic protein/antigen sources that can be included in the vectors of the present invention are listed in US 2004/0241821, which is incorporated herein by reference.

Additional examples of pathogens from which antigens can be obtained are listed in Table 5, below, and specific examples of such antigens include those listed in Table 6. In addition, specific examples of epitopes that can be inserted into the vectors of the invention are provided in Table 7. As is noted in Table 7, epitopes that are used in the vectors of the invention can be B cell epitopes (i.e., neutralizing epitopes) or T cell epitopes (i.e., T helper and cytotoxic T cell-specific epitopes).

The vectors of the invention can be used to deliver antigens in addition to pathogen-derived antigens. For example, the vectors can be used to deliver tumor-associated antigens for use in immunotherapeutic methods against cancer. Numerous tumor-associated antigens are known in the art and can be administered according to the invention. Examples of cancers (and corresponding tumor associated antigens) are as follows: melanoma (NY-ESO-1 protein (specifically CTL epitope located at amino acid positions 157-165), CAMEL, MART 1, gp100, tyrosine-related proteins TRP1 and 2, and MUC1)); adenocarcinoma (ErbB2 protein); colorectal cancer (17-1A, 791Tgp72, and carcinoembryonic antigen); prostate cancer (PSA1 and PSA3). Heat shock protein (hsp110) can also be used as such an antigen. (Also see, e.g., US 2004/0241821 for additional examples.)

In another example of the invention, exogenous proteins that encode an epitope(s) of an allergy-inducing antigen to which an immune response is desired can be used.

The size of the protein or peptide that is inserted into the vectors of the invention can range in length from, for example, from 5-1500 amino acids in length, for example; from 8-1000, 10-500, 10-100, 10-50, 10-35, or 12-20 amino acids in length, as can be determined to be appropriate by those of skill in the art. In addition, the proteins or peptides noted herein can include additional sequences (e.g., 1, 2, 3, 4, 5, 6, 7, 8, 9, or 10 amino acids) or can be reduced in length, also as can be determined to be appropriate by those skilled in the art. Further, as is described elsewhere herein, deletions can be made in the vectors of the invention to accommodate different sized inserts, as determined to be appropriate by those of skill in the art.

Production and Administration

The viruses described above can be made using standard methods in the art. For example, an RNA molecule corresponding to the genome of a virus can be introduced into primary cells, chicken embryos, or diploid cell lines, from which (or from the supernatants of which) progeny virus can then be purified. Other methods that can be used to produce the viruses employ heteroploid cells, such as Vero cells (Yasumura et al., Nihon Rinsho 21:1201-1215, 1963). In an example of such methods, a nucleic acid molecule (e.g., an RNA molecule) corresponding to the genome of a virus is introduced into the heteroploid cells, virus is harvested from the medium in which the cells have been cultured, harvested virus is treated with a nuclease (e.g., an endonuclease that degrades both DNA and RNA, such as BENZONASE™ (endonuclease from *Serratia marcescens*); U.S. Pat. No. 5,173, 418), the nuclease-treated virus is concentrated (e.g., by use of ultrafiltration using a filter having a molecular weight cut-off of, e.g., 500 kDa), and the concentrated virus is formulated for the purposes of vaccination. Details of this method are provided in WO 03/060088 A2, which is incorporated herein by reference. Further, methods for producing chimeric viruses are described in the documents cited above in reference to the construction of chimeric virus constructs.

The vectors of the invention are administered to subjects (e.g., humans and non-human animals, such as horses, livestock, and domestic pets (e.g., cats and dogs)) in amounts and by using methods that can readily be selected by persons of ordinary skill in this art. In the case of chimeric flaviviruses and yellow fever virus-based vectors, the vectors can be administered and formulated, for example, in the same manner as the yellow fever 17D vaccine, e.g., as a clarified suspension of infected chicken embryo tissue, or a fluid harvested from cell cultures infected with the chimeric yellow fever virus. The vectors of the invention can thus be formulated as sterile aqueous solutions containing between 100 and 1,000,000 infectious units (e.g., plaque-forming units or tissue culture infectious doses) in a dose volume of 0.1 to 1.0 ml, to be administered by, for example, intramuscular, subcutaneous, or intradermal routes (see, e.g., WO 2004/0120964 for details concerning intradermal vaccination approaches). In addition, because flaviviruses may be capable of infecting the human host via the mucosal routes, such as the oral route (Gresikova et al., "Tick-borne Encephalitis," In *The Arboviruses, Ecology and Epidemiology*, Monath (ed.), CRC Press, Boca Raton, Fla., 1988, Volume IV, 177-203), the vectors can be administered by a mucosal route. The vectors of the invention can be administered in "effective amounts," which are amounts sufficient to produce a desired effect, such as induction of an immune response (e.g., a specific immune response) and/or amelioration of one or more symptoms of a disease or condition.

When used in immunization methods, the vectors can be administered as primary prophylactic agents in adults or children (or animals; see above) at risk of infection by a particular pathogen. The vectors can also be used as secondary agents for treating infected subjects by stimulating an immune response against the pathogen from which the peptide antigen is derived. Further, an epitope, peptide, or protein is "administered" to a subject according to the methods described herein, whether it is present in the material that is actually administered, or is generated by progeny viruses that replicate from the administered material.

For vaccine applications, optionally, adjuvants that are known to those skilled in the art can be used. Adjuvants that can be used to enhance the immunogenicity of the chimeric vectors include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In the case of a chimeric vector delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the vectors. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses. In addition to vaccine applications, as those skilled in the art can readily understand, the vectors of the invention can be used in gene therapy methods to introduce therapeutic gene products into a patient's cells and in cancer therapy.

The invention also provides methods for producing viral vectors such as those described herein, in which cells (e.g., Vero cells) transfected with RNA corresponding to the vectors are advantageously cultured at a temperature below 37° C., e.g., 30-36° C., 31-35° C., or 32-34° C. As is described further below, culturing of such transfected cells at 34° C. resulted in the production of virus at higher titers, and presumably with a corresponding increase in antigen production, since the antigen is an integral part of the viral envelope protein. Thus, the invention provides an improved method for the production of flavivirus vaccines, such as those described herein.

Experimental Results

CHIMERIVAX™ (a first flavivirus (i.e., a backbone flavivirus) in which a structural protein (or proteins) has been replaced with a corresponding structural protein (or proteins) of a second virus) technology can be used to induce immunity against antigens that are not of flavivirus origin. This requires the insertion of these antigens in the genome of a CHIMERIVAX™ (a first flavivirus (i.e., a backbone flavivirus) in which a structural protein (or proteins) has been replaced with a corresponding structural protein (or proteins) of a second virus) vaccine such as CV-JE, while preserving the viability of the virus and without causing excessive genetic instability. The present invention provides a CHIMERIVAX™ (a first flavivirus (i.e., a backbone flavivirus) in which a structural protein (or proteins) has been replaced with a corresponding structural protein (or proteins) of a second virus)-JE-Influenza vaccine that is viable and appears genetically stable. While CV-JE is normally grown in tissue culture at 37° C., the use of lower incubation temperatures to propagate an engineered virus bearing an inserted antigen in the E protein is shown to improve genetic stability.

An antigen of interest in this study is the M2e epitope of influenza A (strain A/HK/8/68). More specifically, the insert can have the following amino acid sequences: (G)$_{1-2}$MSLLTEVETPIRGG (SEQ ID NO:13 or 15), comprising an N-terminal one- or two-glycine linker, followed by the first 12 amino acids of influenza protein M2, followed in turn by a C-terminal two-glycine linker; and GGMSLLTEVETPIRNEWGSRSNDSSDGG (SEQ ID NO:14), comprising the first 24 amino acids of the influenza M2 protein flanked on both termini with two-glycine linkers. The cDNA encoding these peptides was inserted in the CV-JE genome in such a way that the peptide is: (i) between amino acids 277 and 278 of the E protein ($E_{S275:M2e}$ and E277M2e viruses), or (ii) between amino acids 207 and 208 ($E_{G202:M2e}$ virus). This strategy is generally illustrated in FIG. 1.

Both insertion sites were identified by analysis of structural information of the Japanese encephalitis virus E protein model, which was based on the template of the West Nile virus envelope glycoprotein, in combination with multiple alignment comparisons of the amino acid sequence of Japanese encephalitis with those of several distant members of the Flavivirus family. Table 8 links the names of the constructs with insertion site and insert sequence.

Figure 2B:
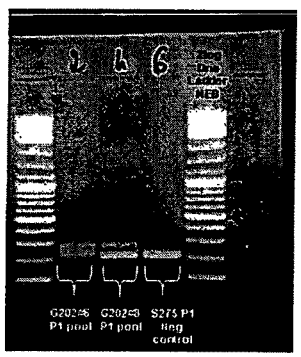
FIG. 2B is an image showing RT-PCR analysis of culture supernatants containing CV-JE in which an M2e peptide was inserted at position 202 of the E protein (E0202:M2e). The insert is detected as a higher molecular weight band (PCR product). Two independent constructs (0202#6 and 0202#8) were tested.

The insertion of the (G)$_{1-2}$MSLLTEVETPIRGG (SEQ ID NO:13 or 15) peptide epitope was carried out, using standard methods, by overlap PCR followed by cloning of the overlap PCR product into plasmid pBSA, which is a bacterial artificial chromosome containing the entire CV-JE genome. The resulting new DNA construct was sequenced according to standard methods to verify that the intended sequence, including the peptide insert, was present. Capped viral genomic RNA was produced by in vitro transcription using the engineered pBSA construct as a template, and this RNA was then transfected into Vero cells using lipofectamine 2000. The transfected cells were grown at 34° C. for 7 days and culture supernatants were harvested (identified as P1) and used to infect fresh culture flasks. After 5 days, these second cultures (P2) were also harvested. In FIG. 2A, RT-PCR analysis of $E_{S275:M2e}$ virus culture supernatants P1 and P2, followed by restriction digestion and agarose gel electrophoresis, reveals the presence of virus containing the insert that had been engineered into the CV-JE genome. The integrity of the insert was confirmed by sequencing of the RT-PCR products. FIG. 2B shows the results of the same procedure carried out on virus supernatants of the $E_{G202:M2e}$ virus. Viral DNA was again detected, however, a mixture of bands was observed, suggesting a mixed population of viruses that either did or did not have the M2e insert at the intended locus.

Figure 3:
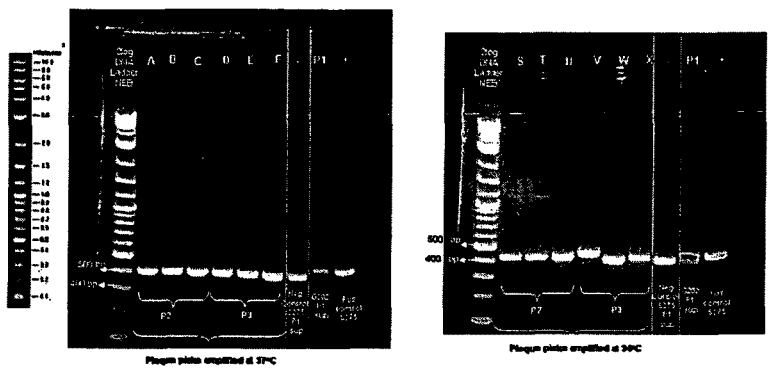
FIG. 3 is a set of images showing RT-PCR analysis of culture supernatants of EG202:M2e plaque picks. Plaques inoculated into cultures grown at 37° C. (left) yielded no insert. When plaques were inoculated into cultures grown at 34° C. (right), one candidate was positive for insert (lane V).

Supernatants P1 and P2 of the $E_{G202:M2e}$ virus were used to infect Vero cells overlaid with agarose to produce plaques. The infected cells were incubated at 34° C. for 5 days, the plaques were then visualized by adding a neutral red-containing overlay for 1 additional day, and 12 individual plaques were picked to isolate single viral clones. These plaque picks were resuspended in a small volume of growth medium and an aliquot of 250 μl was used to inoculate 6 cultures at either 34° C. or 37° C. The cultures were then incubated for 6 days and supernatants harvested. RT-PCR was carried out to determine whether insert-bearing viral isolates were present (FIG. 3). DNA sequencing of RT-PCR product isolated after 4 passages revealed that one residue of the insert was mutated from L to P, yielding the insert sequence GMSLPTEVETPIRGG (SEQ ID NO:33). An amino acid substitution at E protein residue 270 ($E_{1270T}$; wildtype numbering) was also identified.

Figure 4:
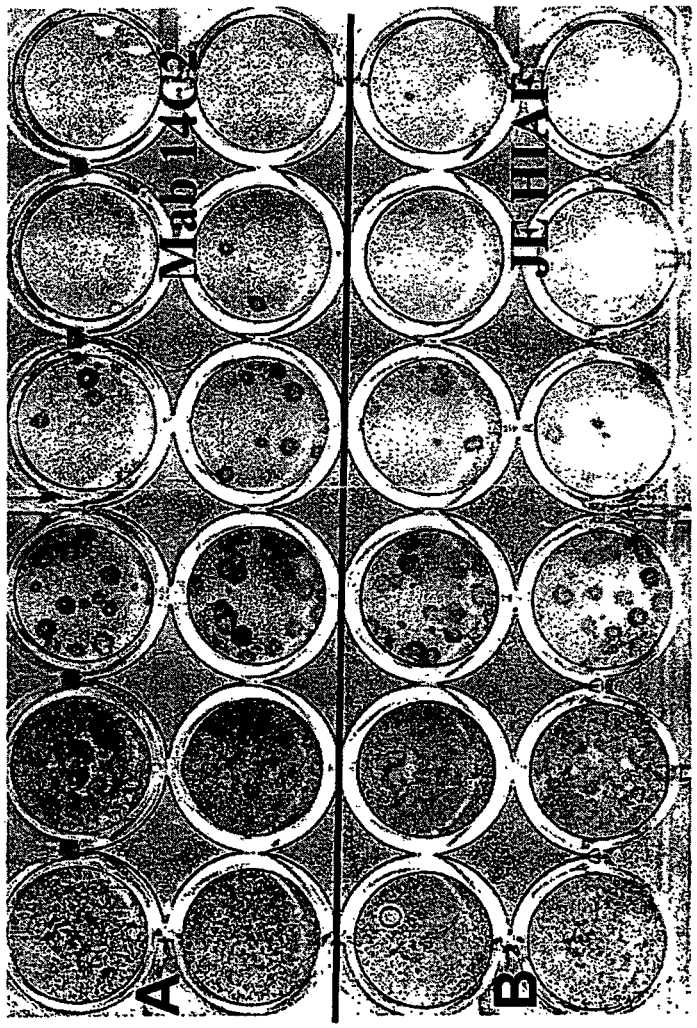
FIG. 4 is a photograph showing viability of CVJE virus with the insert of a M2e epitope between amino acids 277 and 278 of the E protein, and showing M2e expression, as confirmed by immunostaining. Uncloned CVJE-E277M2e virus recovered after RNA transfection of Vero cells was decimally diluted and used to infect confluent Vero monolayers in 24-well plates. After 1 hour of adsorption at 37° C., infected cells were overlaid with methylcellulose maintenance medium and incubated for 4-5 days at 37° C., 5% $CO_2$. To detect foci of virus replication, infected cells were immunostained using: A—Influenza-A αM2 specific mouse Mab 14C2; and B—mouse polyclonal antibodies against Japanese encephalitis virus. There is some plaque heterogeneity of uncloned virus population.

Insertion of GGMSLLTEVETPIRNEWGSRSNDSSDGG (SEQ ID NO:14) peptide at position 277 of Japanese encephalitis virus E protein was carried out essentially using the same methods as described for the (G)$_{1-2}$MSLLTEVETPIRGG (SEQ ID NO:13 or 15) epitope. A DNA fragment derived by overlap PCR was cloned into the pBSA vector, and the presence of insert was confirmed by sequence analysis. Infectious RNA was transcribed from XhoI linearized vector with the insert using the advantage of the SP6 promoter located immediately upstream of the region encoding the full-length genome of CV-JE virus, and used to transfect Vero cells with lipofectamine 2000 reagent. Transfected Vero cells were incubated at 37° C. in the presence of 5% $CO_2$ for 6-7 days until the first sign of cytopathic effect; then culture medium was harvested and an additional round of virus amplification was performed on fresh cells. This resulted in uncloned virus designated as E277M2e herein, which represented a heterologous virus population based on a pattern of plaques developed in Vero cells under methyl cellulose overlay, and stained using a standard immunofocus protocol (FIG. 4). FIG. 4 also demonstrates that all foci produced by E277M2e virus can be equally stained using anti-JE polyclonal antibodies and anti-Influenza A M2 protein monoclonal 14C2 antibody, confirming that the M2e insert is present in most if not all recovered virions.

Figure 6:
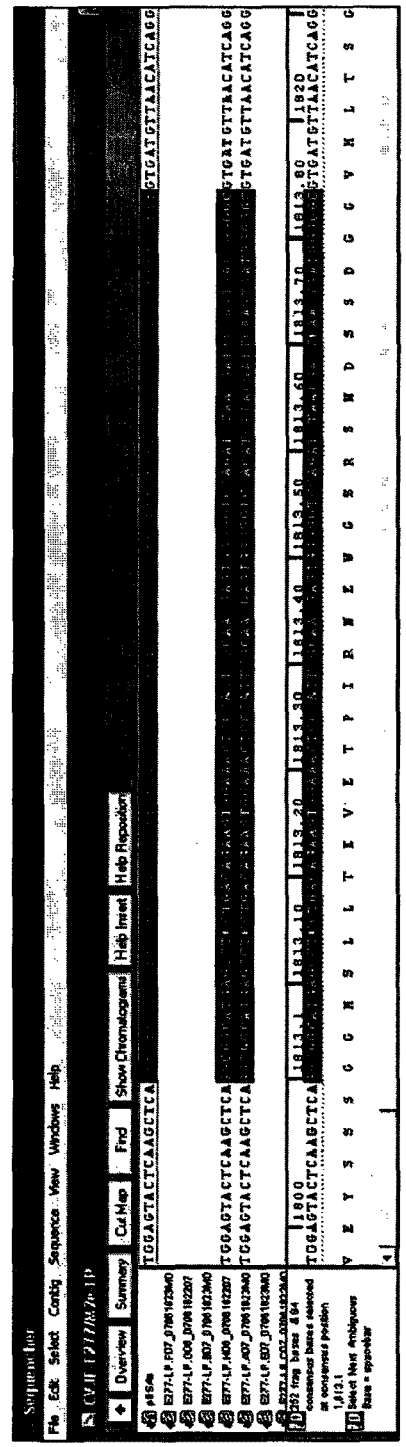
FIG. 6 is a picture showing a sequence analysis of E277M2e-P2 virus, which confirms the presence of an intact M2e insert between amino acids 277 and 288 of E protein (SEQ ID NOs:16-19). Total RNA isolated from Vero cells infected with large plaque (LP) purified E277M2e-P2 was used as a template for RT-PCR amplification of a 5'UTR to NS1 fragment of the virus genome, followed by a sequence reaction using virus-specific primers and the CEQ DTCS-Quick Start Kit, and analyzed on Ceq2000 genetic analyzer (Beckman-Coulter). Sequence chromatograms were assembled with Sequencher 4.2 software, and the window snap-shot with the region surrounding E277 of CVJE is presented. The presence of a DNA fragment encoding an in-frame M2e insert in the E protein gene of E277M2e-P2 virus is highlighted.
Figure 7:
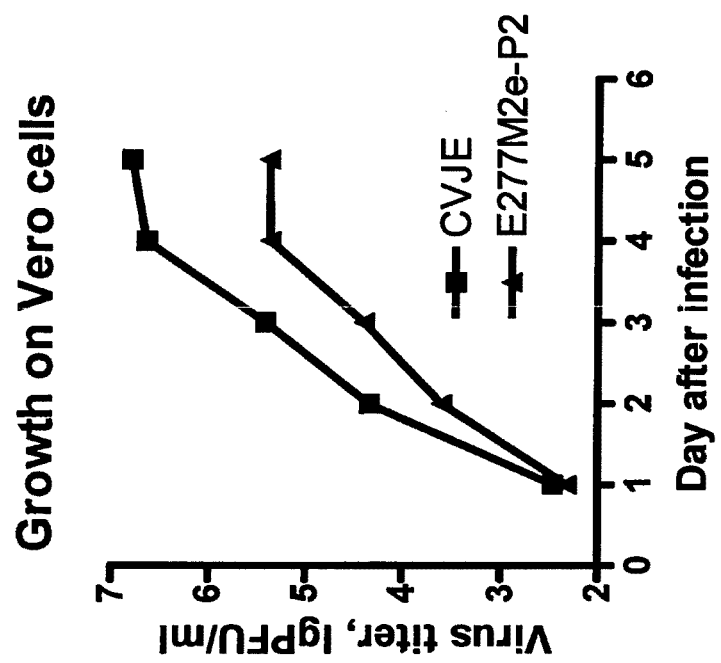
FIG. 7 is a graph illustrating growth of E277M2e-P2 virus and its parent CVJE on Vero cells infected at low 0.001 MOI. One-step growth kinetics of viruses was performed in confluent Vero monolayers in T25 flasks, infected with 0.001 MOI. After 1 hour, virus adsorption cells were supplemented with fresh medium and incubated at 37° C. Equal portions of medium was collected daily and virus titer was analyzed by the immunofocus assay.

Homologous virus was produced by two plaque purifications of E277M2e and selected virus clones were amplified twice on Vero cells to produce a viral stock, identified as P2. One of the E277M2e clones with a large plaque phenotype, designated herein as E277M2e-P2 displayed a uniform plaque morphology on Vero cells, and all foci were equally stained with Mab 14C2 (FIG. 5A). The presence of the M2e insert in-frame in the E protein gene was also confirmed by sequence analysis of an RT-PCR DNA fragment spanning from the 5'-untranslated region to the end of NS1 gene of viral genome (FIG. 6). Stability of M2e insert was confirmed when the E277M2e-P2 virus has undergone 10 passages on Vero cells at low 0.001 MOI, and produced E277M2e-P12 virus, displayed the uniform M2e expression within virus population tested in immunofocus assay (FIG. 5B). Replication of E277M2e-P2 virus on Vero cells was found to be slightly attenuated, nevertheless, by 5 day after infection at 0.001 MOI, as its titer in the medium was only 1 to 1.5 $\log_{10}$ PFU/ml lower when compared to CVJE parental virus (FIG. 7).

Conformation of the M2e epitope and its presence on the surface of the virion when expressed with E protein at position 277 was assayed in a neutralization assay. Monoclonal antibody 14C2, recognizing only a continuous M2e epitope, effectively neutralized E277M2e-P2 virus, with PRNT$_{50}$ titer ≥819,200 (approximately 100 pg of antibody); polyclonal antibody raised against M2e protein within a Hepatitis B core-M2e (HBc-M2e) particle (Acam-FluA vaccine had a similar effect on E277M2e-P2 neutralization, with PRNT$_{50}$ titer of ≥81,920 (FIG. 8). This shows that the M2e insert is expressed on the surface of the E protein of E277M2e-P2, and present in such a conformation on the surface of CVJE virions that makes it accessible for recognition by antibodies.

Figure 9:
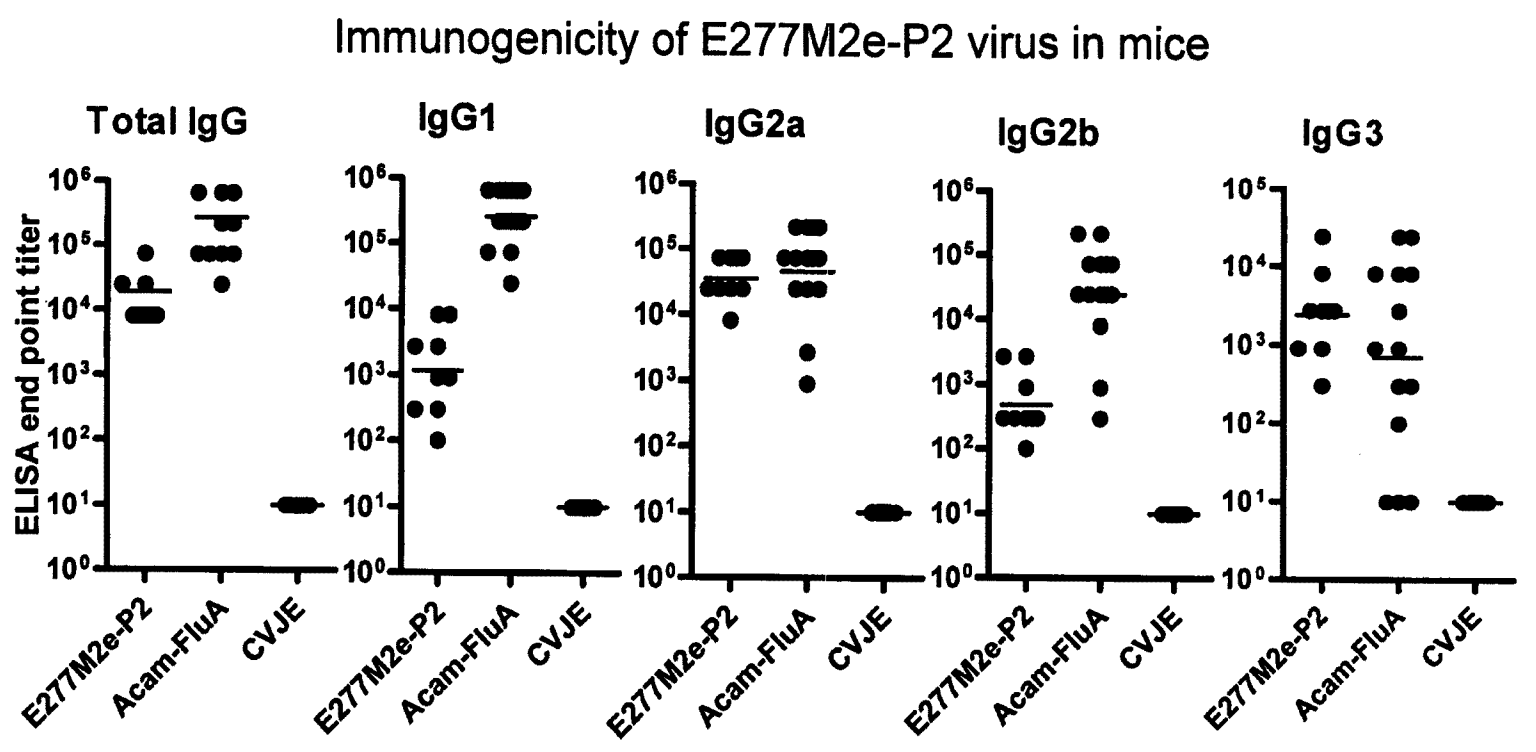

To test the immunogenicity of the M2e epitope delivered by CVJE live virus vector, 4 week old female Balb/C mice in groups of 8-10 animals were intraperitoneally immunized and boosted 30 days after prime with 6 $\log_{10}$ PFU of E77M2e-P2 virus. Two control groups were treated similarly with either 7 $\log_{10}$ PFU/ml of CVJE parental virus or 10 μg of Acam-FluA adjuvanted with aluminum hydroxide. On day 60, after the boosting dose, all animals were bled and humoral immune response was assayed in end-point ELISA against M2e synthetic peptide (FIG. 9). Total IgG response induced by immunization of mice with E277M2e-P2 (approximate titer—1:200,000) was 10-fold lower, as compared to total IgG immunity induced by Acam-FluA. Interestingly, the isotype IgG1/IgG2a antibodies ratio in immune response of mice immunized with Acam-FluA or E277-M2e-P2 did not fall into an even pattern: in E277M2e-P2 group IgG2a antibodies prevailed 100-fold times over IgG1 anti-M2e response, unlike to Acam-FluA immunized mice, where IgG1 isotype was in domination. Such a ratio in IgG1/IgG2a immune response to M2e demonstrates preferable stimulation of the Th1 pathway by E277M2e-P2 virus infection, promoting cell-mediated immunity, shown previously to be of the key components of protection against influenza A infection in mice immunized with M2e based Acam-FluA vaccine.

Figure 10:
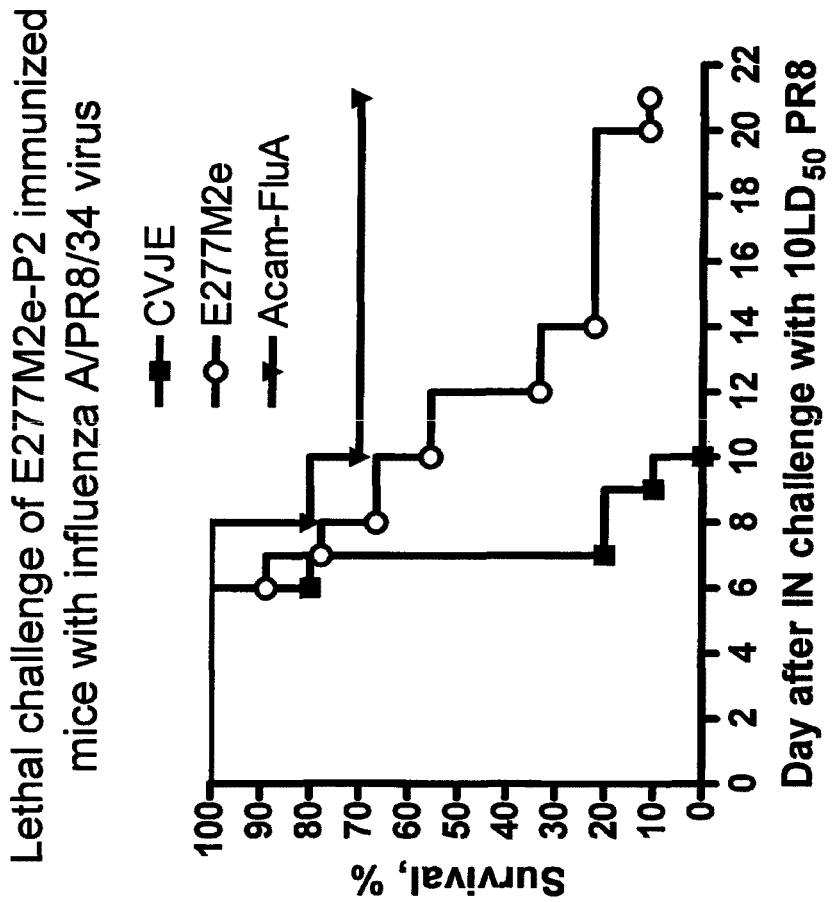
FIG. 10 is a graph showing a protective efficacy of E277M2e-P2 immunized mice against severe challenge with influenza A virus. Balb/C 4 week-old female mice prime/boosted with either CVJE (7 $\log_{10}$ PFU), E277M2e-P2 (6 $\log_{10}$ PFU), or 10 µg of Acam-FluA adjuvanted with Alhydrogel™ were challenged IN on day 60 with 10 $LD_{50}$ of Influenza PR8 virus. Morbidity or mortality was recorded daily and data was plotted as a survival curve. The difference in the survival of the E277M2e-P2 immunized group was statistically significant as compared to CVJE (p=0.0058) and Acam-FluA (p=0.0192) by log rank test, confirming substantial protection against influenza challenge, although less potent when compared to the Acam-FluA vaccine.

Protectivity of induced anti-M2e immunity was challenged for all 3 groups by intranasal infection with 10 $LD_{50}$ of mouse adapted highly pathogenic Influenza A/Puerto Rico8/34 virus on day 60 after immunization with either of E277M2e-P2, CVJE, or Acam-FluA (FIG. 10). Control mice immunized with CVJE parent were not protected and succumbed to lethal infection; and immunization with Acam-FluA protected 70% of mice from influenza challenge. The pattern of survival in the group immunized with E277-P2 did not resemble any of controls: (i) even though only 1 mouse survived the challenge, immunization with E277-M2e-P2 significantly delayed the onset of morbidity, and a significant difference in the survival curve to that of CVJE group was observed (p=0.0058); (ii) however, protection was weaker than that of Acam-FluA immunized group (p=0.0192).

Thus, we demonstrate that viable chimeric flaviviruses can be engineered to display the M2e peptide on their E protein. The present data show that the same inserted peptide (e.g., M2e) may have different effects when inserted at different locations in the E protein. Furthermore, in order to characterize viruses into which epitopes have been inserted, propagation at 34° C. may be advantageous, enabling isolation of single viral clones which can be further characterized, for example by cDNA sequencing and immunization of animals and humans.

TABLE 1

Influenza A virus CTL Epitopes of the Nucleoprotein

| Amino Acid Positions (ref.) | Host | MHC restriction |
|---|---|---|
| 44-52 (ref. 14) | Human | HLA-A1 |
| 50-63 (ref. 3) | Mouse (CBA) | H-2Kk |
| 91-99 (ref. 13) | Human | HLA-Aw68 |
| 147-158 (ref. 5) | Mouse (Balb/c) | H-2Kd |
| 265-273 (ref. 14) | Human | HLA-A3 |
| 335-349 (ref. 1) | Human | HLA-B37 |
| 335-349 (ref. 2) | Mouse | HLA-B37 |
| 365-380 (ref. 2) | Mouse | H-2Db |
| 366-374 (ref. 9) | Mouse (C57B1/6) | H-2Db |
| 380-388 (ref. 16) | Human | HLA-B8 |
| 383-391 (ref. 16) | Human | HLA-B27 |

TABLE 2

Influenza A virus T helper Epitopes of the Nucleoprotein

| Amino Acid Positions (ref.) | Host | MHC restriction |
|---|---|---|
| 55-69 (ref. 8) | Mouse (Balb/c) | H-2Kd |
| 182-205 (ref. 11) | Human | |
| 187-200 (ref. 8) | Mouse (CBA) | H-2Kk |
| | Mouse (Balb/c) | H-2Kd |
| 216-229 (ref. 8) | Mouse (Balb/c) | H-2Kd |
| 206-229 (ref. 11) | Human | HLA-DR1, HLA-DR2 en HLA-DRw13 |
| 260-283 (ref. 8) | Mouse (CBA) | H-2Kk |
| | Mouse (C57B1/6) | H-2Db |
| | Mouse (B10.s) | H-2s |
| 297-318 (ref. 11) | Human | |

TABLE 2-continued

Influenza A virus T helper Epitopes of the Nucleoprotein

| Amino Acid Positions (ref.) | Host | MHC restriction |
|---|---|---|
| 338-347 (ref. 16) | Human | HLA-B37 |
| 341-362 (ref. 11) | Human | |
| 413-435 (ref. 8) | Mouse (C57B1/6) | H-2Db |

TABLE 3

Influenza A Virus T cell Epitopes of Other Viral Proteins

| Peptide | Host | T cell type | MHC restriction |
|---|---|---|---|
| PB1 (591-599) (ref. 14) | Human | CTL | HLA-A3 |
| HA (204-212) (ref. 16) | Mouse | CTL | H-2Kd |
| HA (210-219) (ref. 16) | Mouse | CTL | H-2Kd |
| HA (259-266) (ref. 16) | Mouse | CTL | H-2Kk |
| HA (252-271) (ref. 7) | Mouse | CTL | H-2Kk |
| HA (354-362) (ref. 16) | Mouse | CTL | H-2Kk |
| HA (518-526) (ref. 16) | Mouse | CTL | H-2Kk |
| HA (523-545) (ref. 10) | Mouse | CTL | |
| NA (76-84) (ref. 16) | Mouse | CTL | H-2Dd |
| NA (192-201) (ref. 16) | Mouse | CTL | H-2Kd |
| M1 (17-29) (ref. 6) | Human | T helper | HLA-DR1 |
| M1 (56-68) (ref. 4) | Human | CTL | HLA-A2 |
| M1 (58-66) (ref. 12) | Human | CTL | HLA-A2 |
| M1 (128-135) (ref. 15) | Human | CTL | HLA-B35 |
| NS1 (122-130) (ref. 15) | Human | CTL | HLA-A2 |
| NS1 (152-160) (ref. 16) | Mouse | CTL | H-2Kk |

References
(1) McMichael et al., J. Exp. Med. 164: 1397-1406, 1986.
(2) Townsend et al., Cell 44: 959-968, 1986.
(3) Bastin et al., J. Exp. Med. 165: 1508-1523, 1987.
(4) Gotch et al., Nature 326: 881-882, 1987.
(5) Bodmer et al., Cell 52: 253-258, 1988.
(6) Ceppelini et al., Nature 339: 392-394, 1989.
(7) Sweetser et al., Nature 342: 180-182, 1989.
(8) Gao et al., J. Immunol. 143: 3007-3014, 1989.
(9) Rotzschke et al., Nature 348: 252-254, 1990.
(10) Milligan et al., J. Immunol. 145: 3188-3193, 1990.
(11) Brett et al., J. Immunol. 147: 984-991, 1991.
(12) Bednarek et al., J. Immunol. 147: 4047-4053, 1991.
(13) Cerundolo et al., Proc. Roy. Soc. Lond. Series B boil. Sci. 244: 169-177, 1991.
(14) DiBrino et al., J. Immunol. 151: 5930-5935, 1993.
(15) Dong et al., Eur. J. Immunol. 26: 335-339, 1996.
(16) Parker et al., Seminars in Virology 7: 61-73, 1996.

TABLE 4

Extracellular Part of M2 Protein of Human Influenza A Strains

| Virus strain (subtype) | |
|---|---|
| A/WS/33 (H1N1) | SLLTEVETPIRNEWGCRCNDSSD[1] |
| A/WSN/33 (H1N1) | SLLTEVETPIRNEWGCRCNDSSD |
| A/NWS/33 (H1N1) | SLLTEVETPIRNEWGCRCNDSSD |
| A/PR/8/34 (H1N1) | SLLTEVETPIRNEWECRCNGSSD[2] |
| A/Fort Monmouth/1/47 (H1N1) | SLLTEVETPTKNEWGCRCNDSSD[3] |
| A/fort Warren/1/50 (H1N1) | SLLTEVETPIRNEWGCRCNDSSD |
| A/JapanxBellamy/57 (H2N1) | SLLTEVETPIRNEWGCRCNDSSD |
| A/Singapore/1/57 (H2N2) | SLLTEVETPIRNEWGCRCNDSSD |
| A/Leningrad/134/57 (H2N2) | SLLTEVETPIRNEWGCRCNDSSD |
| A/Ann Harbor/6/60 (H2N2) | SLLTEVETPIRNEWGCRCNDSSD |

TABLE 4-continued

Extracellular Part of M2 Protein of Human Influenza A Strains

| Strain | Sequence |
|---|---|
| A/NT/60/68 (hxNy ?) | SLLTEVETPIRNEWGCRCNDSSD |
| A/Aichi/2/68 (H3N2) | SLLTEVETPIRNEWGCRCNDSSD |
| A/Korea/426/68 (H2N2) | SLLTEVETPIRNEWGCRCNDSSD |
| A/Hong Kong/1/68 (H3N2) | SLLTEVETPIRNEWGCRCNDSSD |
| A/Udorn/72 (H3N2) | SLLTEVETPIRNEWGCRCNDSSD |
| A/Port Chalmers/73 (H3N2) | SLLTEVETPIRNEWGCRCNDSSD |
| A/USSR/90/77 (H1N1) | SLLTEVETPIRNEWGCRCNDSSD |
| A/Bangkok/1/79 | SLLTEVETPIRNEWGCRCNDSSD |
| A/Philippines/2/82/BS (H3N2) | SLLTEVETPIRNEWGCRCNGSSD[2] |
| A/NY/83 (H3N2) | SLLTEVETPIRNEWGCRCNDSSD |
| A/Memphis/8/88 (H3N2) | SLLTEVETPIRNEWGCRCNDSSD |
| A/Beijing/353/89 (H3N2) | SLLTEVETPIRNEWGCRCNDSSD |
| A/Guangdong/39/89 (H3N2) | SLLTEVETPIRNEWGCRCNDSSD |
| A/Kitakyushu/159/93 (H3N2) | SLLTEVETPIRNEWGCRCNDSSD |
| A/Hebei/12/93 (H3N2) | SLLTEVETPIRNEWGCRCNDSSD |
| A/Aichi/69/94 (H3N2) | SLLTEVETPIRNEWECRCNGSSD[4] |
| A/Saga/447/94 (H3N2) | SLLTEVETPIRNEWECRCNGSSD[4] |
| A/Sendai/c182/94 (H3N2) | SLLTEVETPIRNEWGCRCNDSSD |
| A/Akita/1/94 (H3N2) | SLLTEVETPIRNEWGCRCNDSSD |
| A/Sendai/c384/94 (H3N2) | SLLTEVETPIRNEWGCRCNDSSD |
| A/Miyagi/29/95 (H3N2) | SLLTEVETPIRNEWGCRCNDSSD |
| A/Charlottesville/31/95 | SLLTEVETPIRNEWGCRCNDSSD |
| A/Akita/1/95 (H3N2) | SLLTEVETPIRNEWECRCNGSSD[4] |
| A/Shiga/20/95 (H3N2) | SLLTEVETPIRNEWGCRCNDSSD |
| A/Tochigi/44/95 (H3N2) | SLLTEVETPIRNEWECRCNGSSD[4] |
| A/Hebei/19/95 (H3N2) | SLLTEVETPIRNEWECRCNGSSD[4] |
| A/Sendai/c373/95 (H3N2) | SLLTEVETPIRNEWECRCNGSSD[4] |
| A/Niigata/124/95 (H3N2) | SLLTEVETPIRNEWECRCNGSSD[4] |
| A/Ibaraki/1/95 (H3N2) | SLLTEVETPIRNEWECRCNGSSD[4] |
| A/Kagoshima/10/95 (H3N2) | SLLTEVETPIRNEWECRCNGSSD[4] |
| A/Gifu/2/95 (H3N2) | SLLTEVETPIRNEWECRCNGSSD[4] |
| A/Osaka/c1/95 (H3N2) | SLLTEVETPIRNEWECRCNGSSD[4] |
| A/Fukushima/140/96 (H3N2) | SLLTEVETPIRNEWGCRCNDSSD |
| A/Fukushima/114/96 (H3N2) | SLLTEVETPIRNEWGCRCNDSSD |
| A/Niigata/137/96 (H3N2) | SLLTEVETPIRNEWGCRCNDSSD |
| A/Hong Kong/498/97 (H3N2) | SLLTEVETPIRNEWGCRCNDSSD |
| A/Hong Kong/497/97 (H3N2) | SLLTEVETPIRNEWGCRCNDSSD |
| A/Hong Kong/470/97 (H1N1) | SLLTEVETPIRNEWGCRCNDSSD |
| A/Shiga/25/97 (H3N2) | SLLTEVETPIRNEWGCRCNDSSD |
| A/Hong Kong/427/98 (H1N1) | SLLTEVETPIRNEWECRCNDSSD[5] |
| A/Hong Kong/1143/99 (H3N2) | SLLTEVETPIRNEWGCRCNDSSD |
| A/Hong Kong/1144/99 (H3N2) | SLLTEVETPIRNEWGCRCNDSSD |
| A/Hong Kong/1180/99 (H3N2) | SLLTEVETPIRNEWGCRCNDSSD |
| A/Hong Kong/1179/99 (H3N2) | SLLTEVETPIRNEWGCRCNDSSD |

[1] All sequences in this table correspond to SEQ ID NO: 28, except otherwise indicated
[2] SEQ ID NO: 29
[3] SEQ ID NO: 30
[4] SEQ ID NO: 31

TABLE 5

List of examples of pathogens from which epitopes/antigens/peptides can be derived

VIRUSES:

Flaviviridae
  Yellow Fever virus
  Japanese Encephalitis virus
  Dengue virus, types 1, 2, 3 & 4
  West Nile Virus
  Tick Borne Encephalitis virus
  Hepatitis C virus (e.g., genotypes 1a, 1b, 2a, 2b, 2c, 3a, 4a, 4b, 4c, and 4d)
Papoviridae
  Papillomavirus
Retroviridae
  Human Immunodeficiency virus, type I
  Human Immunodeficiency virus, type II
  Simian Immunodeficiency virus
  Human T lymphotropic virus, types I & II
Hepnaviridae
  Hepatitis B virus
Picornaviridae
  Hepatitis A virus
  Rhinovirus
  Poliovirus
Herpesviridae
  Herpes simplex virus, type I
  Herpes simplex virus, type II
  Cytomegalovirus
  Epstein Barr virus
  Varicella-Zoster virus
Togaviridae
  Alphavirus
  Rubella virus
Paramyxoviridae
  Respiratory syncytial virus
  Parainfluenza virus
  Measles virus
  Mumps virus
Orthomyxoviridae
  Influenza virus
Filoviridae
  Marburg virus
  Ebola virus
Rotoviridae
  Rotavirus
Coronaviridae
  Coronavirus
Adenoviridae
  Adenovirus
Rhabdoviridae
  Rabiesvirus

TABLE 5-continued

List of examples of pathogens from which epitopes/antigens/peptides can be derived

BACTERIA:

Enterotoxigenic *E. coli*
Enteropathogenic *E. coli*
*Campylobacter jejuni*
*Helicobacter pylori*
*Salmonella typhi*
*Vibrio cholerae*
*Clostridium difficile*
*Clostridium tetani*
*Streptococccus pyogenes*
*Bordetella pertussis*
*Neisseria meningitides*
*Neisseria gonorrhoea*
*Legionella neumophilus*
*Chlamydial* spp.
*Haemophilus* spp.
*Shigella* spp.
PARASITES:

*Plasmodium* spp.
*Schistosoma* spp.
*Trypanosoma* spp.
*Toxoplasma* spp.
*Cryptosporidia* spp.
*Pneumocystis* spp.
*Leishmania* spp.

TABLE 6

Examples of select antigens from listed viruses

| VIRUS | ANTIGEN |
|---|---|
| Flaviviridae | |
| Yellow Fever virus | Nucleocapsid, M & E glycoproteins |
| Japanese Encephalitis virus | " |
| Dengue virus, types 1, 2, 3 & 4 | " |
| West Nile Virus | " |
| Tick Borne Encephalitis virus | " |
| Hepatitis C virus | Nucleocapsid, E1 & E2 glycoproteins |
| Papoviridae | |
| Papillomavirus | L1 & L2 capsid protein, E6 & E7 transforming protein (oncopgenes) |
| Retroviridae | |
| Human Immunodeficiency virus, type I | gag, pol, vif, tat, vpu, env, nef |
| Human Immunodeficiency virus, type II | " |
| Simian Immunodeficiency virus | " |
| Human T lymphotropic virus, types I & II | gag, pol, env |

TABLE 7

Examples of B and T cell epitopes from listed viruses/antigens

| VIRUS | ANTIGEN | EPITOPE | LOCATION | SEQUENCE (5'-3') |
|---|---|---|---|---|
| Flaviviridae | | | | |
| Hepatitis C | Nucleocapsid | CTL | 2-9 | STNPKPQR (SEQ ID NO: 34) |
| | | | 35-44 | YLLPRRGPRL (SEQ ID NO: 35) |
| | | | 41-49 | GPRLGVRAT (SEQ ID NO: 36) |
| | | | 81-100 | YPWPLYGNEGCGWAGWLLSP (SEQ ID NO: 37) |
| | | | 129-144 | GFADLMGYIPLVGAPL (SEQ ID NO: 38) |
| | | | 132-140 | DLMGYIPLV (SEQ ID NO: 39) |
| | | | 178-187 | LLALLSCLTV (SEQ ID NO: 40) |
| | E1 glycoprotein | CTL | 231-250 | REGNASRCWVAVTPTVATRD (SEQ ID NO: 41) |
| | E2 glycoprotein | CTL | 686-694 | STGLIHLHQ (SEQ ID NO: 42) |
| | | | 725-734 | LLADARVCSC (SEQ ID NO: 43) |
| | | | 489-496 | CWHYPPRPCGI (SEQ ID NO: 44) |
| | | | 569-578 | CVIGGVGNNT (SEQ ID NO: 45) |
| | | | 460-469 | RRLTDFAQGW (SEQ ID NO: 46) |
| | | | 621-628 | TINYTIFK (SEQ ID NO: 47) |

TABLE 7-continued

Examples of B and T cell epitopes from listed viruses/antigens

| VIRUS | ANTIGEN | EPITOPE | LOCATION | SEQUENCE (5'-3') |
|---|---|---|---|---|
| | | B cell | 384-410 | ETHVTGGNAGRTTAGL VGLLTPGAKQN (SEQ ID NO: 48) |
| | | | 411-437 | IQLININGSWHINSTA LNCNESLNTGW (SEQ ID NO: 49) |
| | | | 441-460 | LFYQHKFNSSGCPERL ASCR (SEQ ID NO: 50) |
| | | | 511-546 | PSPVVVGTTDRSGAPT YSWG ANDTDVFVLNNTRPPL (SEQ ID NO: 51) |
| | | T helper | 411-416 | IQLINT (SEQ ID NO: 52) |
| Papoviridae | | | | |
| HPV 16 | E7 | T helper | 48-54 | DRAHYNI (SEQ ID NO: 53) |
| | | CTL | 49-57 | RAHYNIVTF (SEQ ID NO: 54) |
| | | B cell | 10-14 | EYMLD (SEQ ID NO: 55) |
| | | | 38-41 | IDGP (SEQ ID NO: 56) |
| | | | 44-48 | QAEPD (SEQ ID NO: 57) |
| HPV 18 | E7 | T helper | 44-55 | VNHQHLPARRA (SEQ ID NO: 58) |
| | | | 81-90 | DDLRAFQQLF (SEQ ID NO: 59) |

TABLE 8

Nomenclature of CV-JE influenza epitope insertion clones

| | Insertion site | Inserted sequence |
|---|---|---|
| $E_{G202:M2e}$ | After G207 in JE E | GMSLLTEVETPIRGG (SEQ ID NO: 13) |
| $E_{S275:M2e}$ | After S277 in JE E | GGMSLLTEVETPIRGG (SEQ ID NO: 14) |

The contents of all references cited above are incorporated herein by reference. Use of singular forms herein, such as "a" and "the," does not exclude indication of the corresponding plural form, unless the context indicates to the contrary. Thus, for example, if a claim indicates the administration of "a" flavivirus, it can also be interpreted as covering administration of more than one flavivirus, unless otherwise indicated. Other embodiments are within the following claims.

What is claimed is:

1. A flavivirus comprising an insertion of sequences encoding a heterologous peptide or protein between nucleotides encoding amino acids corresponding to amino acids 277 and 278 of the envelope protein of Japanese encephalitis virus (SEQ ID NO: 60).

2. The flavivirus of claim 1, wherein the flavivirus is a chimeric flavivirus comprising structural sequences of a first flavivirus and non-structural sequences of a second flavivirus.

3. The flavivirus of claim 2, comprising pre-membrane and envelope sequences of said first flavivirus and capsid and non-structural sequences of said second flavivirus.

4. The flavivirus of claim 2, wherein said second flavivirus is a yellow fever virus.

5. The flavivirus of claim 2, wherein said first flavivirus is selected from the group consisting of: Japanese encephalitis, Dengue-1, Dengue-2, Dengue-3, Dengue-4, Murray Valley encephalitis, St. Louis encephalitis, West Nile, Kunjin, Rocio encephalitis, Ilheus, Tick-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

6. The flavivirus of claim 1, wherein the heterologous peptide or protein is an antigen.

7. The flavivirus of claim 6, wherein the antigen is derived from an infectious agent.

8. The flavivirus of claim 7, wherein the infectious agent is an influenza virus.

9. The flavivirus of claim 8, wherein the antigen is selected from the group consisting of hemagglutinin, neuraminidase, or M2, or an immunogenic fragment thereof.

10. The flavivirus of claim 9, wherein the M2 antigen comprises the M2e region of the M2 protein or a fragment thereof.

11. The flavivirus of claim 10, wherein the antigen comprises a peptide of the sequence MSLLTEVETPIR (SEQ ID NO:1) or MSLLTEVETPIRNEWGSRSNDSSD (SEQ ID NO:2).

12. The flavivirus of claim 11, wherein the antigen comprises amino and/or carboxy terminal glycine linker sequences.

13. The flavivirus of claim 1, wherein the heterologous peptide or protein comprises a sequence of SEQ ID NO: 14.

14. The flavivirus of claim 1, comprising a deletion in 3'-untranslated region or the NS1 sequences.

15. A nucleic acid molecule encoding the flavivirus of claim 1, or the complement thereof.

16. A pharmaceutical composition comprising a flavivirus of claim 2 and a pharmaceutically acceptable carrier or diluent.

17. A method of producing a flavivirus, comprising culturing Vero cells into which RNA corresponding to the virus has been introduced at a temperature below 37° C., wherein the flavivirus comprises an insertion of sequences encoding a heterologous peptide or protein between nucleotides encoding amino acids corresponding to amino acids 277 and 278 of the envelope protein of Japanese encephalitis virus (SEQ ID NO: 60).

18. A method of propagating a flavivirus, comprising incubating Vero cells infected with said flavivirus at a temperature below 37° C., wherein the flavivirus comprises an insertion of sequences encoding a heterologous peptide or protein between nucleotides encoding amino acids corresponding to amino acids 277 and 278 of the envelope protein of Japanese encephalitis virus (SEQ ID NO: 60).

19. A flavivirus replicon comprising an insertion of sequences encoding a heterologous peptide or protein between nucleotides encoding amino acids corresponding to amino acids 277 and 278 of the envelope protein of Japanese encephalitis virus (SEQ ID NO: 60).

* * * * *